(12) United States Patent
Monjo Cabrer et al.

(10) Patent No.: US 9,433,710 B2
(45) Date of Patent: Sep. 6, 2016

(54) BIOCOMPATIBLE IMPLANT

(71) Applicants: LABORATORIS SANIFIT, S. L., Palma de Mallorca (ES); NUMAT BIOMEDICAL, S. L., Palma de Mallorca (ES)

(72) Inventors: Marta Monjo Cabrer, Palma de Mallorca (ES); Joan Perelló Bestard, Palma de Mallorca (ES); Joana María Ramis Morey, Palma de Mallorca (ES); Fernando Tur Espinosa, Palma de Mallorca (ES); María del Mar Arriero Sánchez, Palma de Mallorca (ES); Eva Martín Becerra, Palma de Mallorca (ES); Bernat Isern Amengual, Palma de Mallorca (ES); Rubén Henríquez Paláez, Palma de Mallorca (ES)

(73) Assignees: LABORATORIES SANIFIT, S. L., Palma de Mallorca (ES); NUMAT BIOMEDICAL, S. L., Palma de Mallorca (ES)

( * ) Notice: Subject to any disclaimer, the term of this patent is extended or adjusted under 35 U.S.C. 154(b) by 0 days.

(21) Appl. No.: 14/365,545

(22) PCT Filed: Dec. 26, 2012

(86) PCT No.: PCT/EP2012/076906
§ 371 (c)(1),
(2) Date: Jun. 13, 2014

(87) PCT Pub. No.: WO2013/098295
PCT Pub. Date: Jul. 4, 2013

(65) Prior Publication Data
US 2015/0004208 A1 Jan. 1, 2015

(30) Foreign Application Priority Data

Dec. 26, 2011 (EP) .................................. 11382404

(51) Int. Cl.
| A61L 31/02 | (2006.01) |
| A61L 27/12 | (2006.01) |
| A61F 2/30 | (2006.01) |
| A61F 2/28 | (2006.01) |
| A61L 31/16 | (2006.01) |
| A61L 27/50 | (2006.01) |
| A61L 27/54 | (2006.01) |
| A61L 27/04 | (2006.01) |
| A61L 27/06 | (2006.01) |
| A61L 31/14 | (2006.01) |
| A61L 31/08 | (2006.01) |

(52) U.S. Cl.
CPC ............... *A61L 31/16* (2013.01); *A61L 27/04* (2013.01); *A61L 27/06* (2013.01); *A61L 27/50* (2013.01); *A61L 27/54* (2013.01); *A61L 31/022* (2013.01); *A61L 31/08* (2013.01); *A61L 31/14* (2013.01); *A61L 2300/112* (2013.01); *A61L 2300/40* (2013.01); *A61L 2300/412* (2013.01); *A61L 2300/606* (2013.01); *A61L 2400/18* (2013.01); *A61L 2420/02* (2013.01); *A61L 2430/02* (2013.01)

(58) Field of Classification Search
None
See application file for complete search history.

(56) References Cited

U.S. PATENT DOCUMENTS

| 5,478,237 | A | 12/1995 | Ishizawa | |
| 5,782,908 | A * | 7/1998 | Cahalan | A61L 27/28 424/422 |
| 2011/0046747 | A1* | 2/2011 | Yeung | A61L 27/06 623/23.6 |
| 2012/0064132 | A1* | 3/2012 | Aizawa et al. | 424/400 |

FOREIGN PATENT DOCUMENTS

| JP | WO 2010134638 A1 * | 11/2010 | ............. A61L 27/12 |
| WO | WO 2004/024202 | 3/2004 | |
| WO | WO-2004024202 | 3/2004 | |
| WO | WO 2009/158325 | 12/2009 | |
| WO | WO-2009158325 | 12/2009 | |
| WO | WO 2009158325 A2 * | 12/2009 | ........... A61L 31/022 |

(Continued)

OTHER PUBLICATIONS

PCT Search Report; PCT/EP2012/076906 dated Jun. 11, 2013.
EP Search Report; EP Appl No. 11382404; May 24, 2012.
Grases, Felix, et al., "Effect of Tetracalcium Dimagnesium Phytate on Bone Characteristics in Ovariectomized Rats", *Journal of Medicine Food*; pp. 1301-1306; Jun. 2009.
Liu, Xuanyong, et al., "Surface modification of titanium, titanium alloys, and related materials for biomedical applications", *Materials Science and Engineering R 47; Reports: A Review Journal*; 2004 Elsevier; pp. 49-121.
Mills, Andrew, et al., "An overview of semiconductor photocatalysis", *Journal of Photochemistry and Photobiology A: Chemistry* 108 (1997) pp. 1-35.

(Continued)

Primary Examiner — H. Sarah Park
(74) Attorney, Agent, or Firm — Blakely Sokoloff Taylor & Zafman LLP

(57) ABSTRACT

The present invention relates to a biocompatible implant comprising one or more metal(s), metal alloy(s), metal oxide(s) or a combination thereof, wherein a compound selected from the group consisting of an IP, an ester of an IP, and/or a pharmaceutically acceptable salt thereof, or a combination thereof, is/are covalently bound to at least a part of a metal, metal alloy or metal oxide surface of said biocompatible implant. The covalent bond between the IP and the metal, metal alloy or metal oxide surface can be further assisted by the use of a linker. An implant according to the invention provides for a modulated and/or improved osseointegrative effect when implanted into a body, such as a mammalian body, by virtue of the coating comprising covalently bound phytate.

18 Claims, 13 Drawing Sheets

(56) References Cited

FOREIGN PATENT DOCUMENTS

| WO | WO 2010/134638 | 11/2010 |
|---|---|---|
| WO | WO-20100134638 | 11/2010 |

OTHER PUBLICATIONS

Miyauchi, Masahiro, et al., "Reversible wettability control of TiO2 surface by light irradiation", *Surface Science* 511; pp. 401-407; 2002.

Nakamura, Masatoshi, et al., "Study on hydrolic property of hydro-oxegenated amorphous TiOx: OH thin films", *Surface Science* 507-510; pp. 778-782; 2002.

Petzold, Christiane, et al., "UV-induced chemical coating of titanium surfaces with eicosapentaenoic acid", www.rsc.org/materials; *Journal of Materials Chemistry*; pp. 5502-5510; 2008.

Wang, Rong, et al., "Photogeneration of HIghly Amphiphilic TiO2 Surfaces", *Adv. Mater*, 2998; 10, No. 2 pp. 135-138.

Wu, Kee-Rong, et al., "Deposition of graded TiO2 films featured both hydrophobic and photo-induced hydrophilic properties", *Science Direct; Applied Surface Science* 252; pp. 5829-5838; 2006.

\* cited by examiner

A

RANKL    -        +        +

IP6       -        -        +

A

B

BIOCOMPATIBLE IMPLANT

CROSS-REFERENCE TO RELATED APPLICATIONS

The present patent application is a national phase application of International Application No. PCT/EP2012/076906, filed Dec. 26, 2012, which application claims priority to European Application No. 11382404.9, filed Dec. 26, 2011.

FIELD OF THE INVENTION

The present invention relates to the field of biocompatible implants, in particular biocompatible implants comprising at least one metal such as titanium, zirconium, tantalum, hafnium, niobium, chromium-vanadium alloy and stainless steel, or an alloy thereof. More specifically, the present invention relates to biocompatible implants comprising a metal, metal alloy and/or metal oxide surface which comprises a coating providing for modulated and/or improved osseointegration of said biocompatible implant when implanted into a mammalian body.

BACKGROUND TO THE INVENTION

Medical implants, such as dental implants, orthopaedic implants, prosthesis and vascular stents are commonly made of titanium and/or a titanium alloy. Titanium is the material most frequently used as implant in bone, as it has outstanding physical and biological properties, such as low density, mechanical strength, and chemical resistance against body fluids. Titanium is a well-known biocompatible material, successfully used for the manufacturing of prostheses and dental implants. Its surface chemistry and structure are prime factors governing bone integration.

Dental implants are utilized in dental restoration procedures in patients having lost one or more of their teeth. A dental implant comprises a dental fixture, which is utilized as an artificial tooth root replacement. Thus, the dental fixture serves as a root for a new tooth. Typically, the dental fixture is a titanium screw which has a roughened surface in order to expand the area of tissue contact. The titanium screw is surgically implanted into the jawbone, where after the bone tissue grows around the screw. This process is called osseointegration, because osteoblasts grow on and into the rough surface of the implanted screw. By means of osseointegration, a rigid installation of the screw is obtained.

Once the titanium screw is firmly anchored in the jawbone, it may be prolonged by attachment of an abutment to the screw. The abutment may, just as the screw, be made of titanium or a titanium alloy. The shape and size of the utilized abutment are adjusted such that it precisely reaches up through the gingiva after attachment to the screw. A dental restoration such as a crown, bridge or denture may then be attached to the abutment. Alternatively, the titanium screw has such a shape and size that it reaches up through the gingiva after implantation, whereby no abutment is needed and a dental restoration such as a crown, bridge or denture may be attached directly to the screw.

Orthopedic implants are utilized for the preservation and restoration of the function in the musculoskeletal system, particularly joints and bones, including alleviation of pain in these structures. Vascular stents are tubular implants arranged for insertion into blood vessels in order to prevent or counteract a localized flow constriction, i.e. they counteract significant decreases in blood vessel diameter.

As already mentioned above, titanium (Ti) is commonly used in dental and orthopaedic applications and in vascular stents. The stable oxides that form readily on Ti surfaces have been reported to attribute to its excellent biocompatibility. However, it has also been reported that bone response to implant surfaces was dependent on the chemical and physical properties of Ti surfaces, thereby affecting implant success. As such, attention has been focused on the surface preparation of Ti implants.

As the surface of titanium and its alloys are bioinert, a fibrous tissue of variable thickness may form, encapsulating and isolating the implants from the surrounding environment when they are used for osseointegration. This lack of osseointegration is being addressed through the modification of the implant surface by bonding bioactive coatings. Current research on modification of implant surfaces focuses on making virtual bioinert materials become bioactive, or rather to influence the types of proteins absorbed at the surface readily after implantation. The assortment of surface modifications ranges from non-biological coatings, such as carbide, fluorine, calcium, hydroxyl apatite or calcium phosphate, to coatings that are to mimic the biological surroundings using lipid mono- or bi-layers, growth factors, proteins, and/or peptides.

The biocompatibility of prostheses or implants has been proposed to improve by binding or integrating various active biomolecules to the surface of the prosthesis, e.g. on to the metallic surface of a titanium prosthesis. It has been the aim with implants prepared this way that they have improved fit; exhibit increased tissue stickiness and increased tissue compatibility; have a biologically active surface for increased cell growth, differentiation and maturation; exhibit reduced immunoreactivity; exhibit antimicrobial activity; exhibit increased biomineralisation capabilities; result in improved wound and/or bone healing; lead to improved bone density; have reduced "time to load" and cause less inflammation.

Various surface mechanical, chemical, and physical surface modification methods have been applied to titanium alloys including machining or polishing, acidic or alkaline treatment, anodic oxidation, chemical vapor deposition, biochemical modification through silanization, physical vapor deposition, ion implantation, and glow discharge plasma treatment. For biological applications, plasma treatment using radio frequency glow discharge (RFGD) is especially attractive as it may be used to deposit active functional groups for covalent attachment of other polymers or biomolecules. Similarly, silane coupling agents with a terminal functional group have been used for surface modification of inorganic silicas as well as metallic materials. Others have reported the modification of titanium surfaces by alkylsilanes to form organic films with good stability, furthermore, coupling agents such as organofunctional trialkoxysilanes have been applied to form durable chemical bonding between inorganic and organic molecules (or moieties) (Liu. Chu et al. 2004 ).

However, inositol phosphates (IPs) have never been reported to be covalently attached to the metal surface, directly or through a linker.

Myo-inositol-1,2,3,4,5,6-hexakisphosphate (IP6 ), also known as phytic acid or phytate (when in a salt form) is a molecule abundant in vegetable seeds and legumes. It is also naturally present in all mammalian biological fluids (e.g. urine and plasma) due to exogenous administration, mainly dietary ingestion. Several potential beneficial effects of this compound on human health have recently been demonstrated. In particular, IP6 functions as an inhibitor of bone resorption in animal models of osteoporosis. It is adsorbed on the surface of hydroxyapatite (HAP), the mineral constituent of bone, decreasing the progressive loss of bone mass acting as a potent inhibitor of hydroxyapatite dissolution.

The structure of IPs and their affinity for calcium ions give them properties as crystallization inhibitors, as well as antiresorptive properties (Grases. Sanchis et al. 2010).

Phytate has previously been described in the context of biocompatible medical implants, such as e.g. in WO2004/024202, which disclose biocompatible implants having a coating of a phosphoric containing metal oxide which is formed by an anodic treatment. The coating is added to the implant to facilitate its attachment to bone tissue.

Furthermore, in U.S. Pat. No. 5,478,237, similar to WO 2004/024202, implants are also produced by anodic treatment. The coatings on the implants presented additionally comprise Ca and P ions for improving bone growth to the implant described therein.

However, anodic treatment does not produce covalent binding of the biomolecules, but involves the formation of an adsorbed film layer containing oxygen and the biomolecules (with Ca and P, for example) on the metal surface.

Despite the availability of biocompatible implants in the art today, there is still a need to to identify alternative biocompatible implants which further may facilitate osseointegration of an implant when introduced into a mammalian body. Accordingly, an object of the present invention is to overcome some of the problems associated with the implants of the prior art, which are mainly related to the difficulties of permanently binding bioactive molecules to an implant surface. Furthermore, there is a limitation of most of the available techniques with regards to the physical absorption (labile union) of these compounds onto the surface of the implant.

SUMMARY OF THE INVENTION

The above presented objects have now been at least mitigated by a biocompatible implant comprising one or more metal(s), metal alloy(s), metal oxide(s) or a combination thereof, wherein a compound selected from the group consisting of an inositol phosphate (IP), an ester of an IP, and/or a pharmaceutically acceptable salt thereof, or a combination thereof, is/are covalently bound to at least a part of a metal, metal alloy or metal oxide surface of said biocompatible implant. The invention also relates to a biocompatible implant comprising titanium and/or a titanium alloy, wherein a compound selected from the group consisting of an IP, an ester of an IP, and/or a pharmaceutically acceptable salt thereof, or a combination thereof, is/are covalently bound to at least a part of a metal, metal alloy or metal oxide surface of said biocompatible implant.

Accordingly, the present inventors have now surprisingly found that by covalently binding an IP, an ester of an IP, and/or a pharmaceutically acceptable salt thereof and/or a combination thereof to a metal, metal alloy or metal oxide surface, such as a titanium and/or a titanium alloy surface, of a biocompatible implant, the osseointegrating properties of the implant may be greatly facilitated. Such a biocompatible implant has not previously been known nor implied within the field.

The present invention furthermore relates to a biocompatible implant wherein a linker is used, such as a silicon linker, to form a covalent bond between the surface of the implant and said IP, an ester of an IP, and/or a pharmaceutically acceptable salt thereof, or combination thereof. In such an aspect, one part of said linker is bound to said surface, and another part of the linker is bound to said IP, ester of an IP, and/or pharmaceutically acceptable salt thereof, or combination thereof, thereby forming a covalent bond between the IP and the surface. The bond between the linker and said surface and said IP, ester of an IP, a pharmaceutically acceptable salt thereof, or combination thereof, is effected by chemical reactions occurring between the linker and the IP thereby securing a covalent bond between the surface and said IP and/or ester of IP. Such an event is illustrated e.g. in FIG. 1 or 2.

The present invention also relates to a method for producing a biocompatible implant comprising adding an IP, an ester of an IP, and/or a pharmaceutically acceptable salt thereof or a combination thereof to a metal, metal alloy or metal oxide surface of said biocompatible implant, which method may optionally comprise chemically pre-treating said biocompatible implant before adding an IP, an ester of a phytate, and/or a pharmaceutically acceptable salt thereof or combination thereof, to said chemically pre-treated implant. Said method can also comprise a step of adding a linker, such as a silicon linker, optionally after a chemical pre-treatment of said implant and before adding said IP to the biocompatible implant.

In further aspects, the invention also relates to a biocompatible implant obtainable by a method as defined herein, as well as to a method for introducing a biocompatible implant into a patient in need thereof.

Further aspects/embodiments of the present invention can be found in the following clauses:

Clause 1. A biocompatible implant comprising one or more metal(s), metal alloy(s), metal oxide(s) or a combination thereof, wherein a compound selected from the group consisting of an IP, an ester of an IP, and/or a pharmaceutically acceptable salt thereof, or a combination thereof, is/are covalently bound, with or without a linker, to at least a part of a metal, metal alloy or metal oxide surface of said biocompatible implant.

Clause 2. A biocompatible implant according to clause 1, wherein the IP comprises 1, 2, 3, 4, 5 or 6 phosphate groups, such as inositol hexaphosphate (IP6).

Clause 3. A biocompatible implant according to clause 1, wherein at least 50% of weight of said IP, ester of IP, and/or pharmaceutically acceptable salt and/or combination thereof present on said metal, metal alloy or metal oxide surface of said biocompatible implant is covalently bound to said surface Clause 4. A biocompatible implant according to any one of the preceding clauses, wherein at least 60% of said IP, ester of IP, and/or pharmaceutically acceptable salt thereof, or combination thereof, present on said a metal, metal alloy or metal oxide surface of said biocompatible implant is covalently bound thereto, such as at least 70 or 80%.

Clause 5. A biocompatible implant according to any one of the preceding clauses, wherein a linker is bound to said a metal, metal alloy or metal oxide surface and to said IP, ester of an IP, and/or a pharmaceutically acceptable salt thereof, or a combination thereof.

Clause 6. A biocompatible implant according to clause 5, wherein said linker is selected from the group consisting of anhydrides, alcohols, acids, amines, epoxies, isocyanates, silanes, halogenated groups, and polymerizable groups, preferably 3-aminopropyltriethoxysilane (APTES).

Clause 7. A biocompatible implant according to any one of the preceding clauses, wherein said metal(s), metal alloy(s), metal oxide(s) or a combination thereof is/are selected from the group consisting of titanium, an alloy or an oxide thereof; zirconium, an alloy or an oxide thereof;

tantalum, an alloy or an oxide thereof; hafnium, an alloy or an oxide thereof, niobium, an alloy or an oxide thereof; chromium-vanadium alloy and/or a combined oxide and stainless steel, preferably titanium, titanium oxide or an alloy thereof.

Clause 8. A biocompatible implant according to any one of the preceding clauses, wherein the implant is selected from the group consisting of a surgical implant, an orthopedic implant, a dental implant, an orthopedic fixation device, an orthopedic joint replacement, a prosthetic disc for spinal fixation and a metal. Said implant can also be a metal graft material, preferably a metal oxide scaffold comprising titanium oxide.

Clause 9. A biocompatible implant according to any one of the preceding clauses, wherein other biomolecules are present on a metal and/or metal alloy surface of the implant, said biomolecules being selected from the group consisting of natural biomolecules, synthetic biomolecules, and recombinant biomolecules, such as bioadhesives, cell attachment factors, biopolymers, blood proteins, enzymes, extracellular matrix proteins and biomolecules, growth factors and hormones, nucleic acids (DNA and RNA), receptors, synthetic biomolecules, vitamins, drugs, biphosphonates, biologically active ions, fluoride, and marker biomolecules.

Clause 10. A method for producing a biocompatible implant according to any one of the preceding clauses, comprising contacting and reacting an IP, an ester of an IP, and/or a pharmaceutically acceptable salt thereof, or a combination thereof, with the surface of said biocompatible implant.

Clause 11. A method according to clause 10, comprising the steps of:
a) chemically pre-treating the surface of an implant.
b) contacting and reacting an IP, an ester of an IP, and/or a pharmaceutically acceptable salt thereof, or a combination thereof, with said chemically pre-treated surface.

Clause 12. A method according to clause 11, wherein before step b), a step of contacting and reacting a linker with said chemically pre-treated surface obtained in step a) is performed, and wherein in step b) IP is reacted with said linker.

Clause 13. A method according to any one of clause 10-11, wherein step a) is performed by a passivation treatment, a piranha treatment or by treatment with one or more alkali solution(s).

Clause 14. A method according to any one of clauses 11-13, wherein said IP, ester of IP, pharmaceutically acceptable salt thereof or combination thereof is/are activated before being added to the surface in step b).

Clause 15. A method according to clause 14, wherein said activation is performed by adding a carbodiimide crosslinker, such as N-(3-dimethylaminopropyl)-N'-ethylcarbodiimide (EDC), to said IP, ester of IP, pharmaceutically acceptable salt thereof, or combination thereof.

Clause 16. A method according to any one of clauses 14-15, wherein the activation comprises the formation of a phosphoramidate.

Clause 17. A method according to clause 16, wherein the formation of a phosphoramidate comprises the following steps:
a) adding 1-ethyl-3-3-dimethiylaminopropylcarbodimide hydrochloride to said phytateinositol phosphate, ester of an inositol phosphate phytate, pharmaceutically acceptable salt thereof, or combination thereof, for the formation of an active ester, and thereafter
b) adding imidazole to said active ester for the formation of an active phosphoramidate.

Clause 18, A biocompatible implant obtainable by a method according to any one of clauses 10-17.

Clause 19. Use of a biocompatible implant according to any one of clauses 1-9 and 18 for its use in the modulation and/or improvement of osseointegration.

Clause 20. A biocompatible implant according to any one of clauses 1-9 and 18 for its use in regenerative medicine, preferably to replace bone tissue and/or restore a function of the body of a vertebrate animal, in particular a mammal, such as a human.

Clause 21. A method for introducing a biocompatible implant into a patient in need thereof, said method comprising the steps of:
a) providing an implant as defined in any one of clauses 1-9, or 18 and,
b) introducing said implant into said patient by a surgical procedure.

DETAILED DESCRIPTION OF THE INVENTION

Accordingly, the present invention relates to a biocompatible implant providing for modulated, preferably improved, osseointegrating properties due to the physical characteristics of a metal, metal alloy, metal oxide or a combination thereof surface layer comprising an IP bound thereto. Such an advantageous surface layer was prepared by covalently binding an IP to a metal, metal alloy or metal oxide surface, such as a titanium, titanium alloy or titanium oxide surface of said implant, thereby obtaining a surface which is suitable for osseointegration.

Hence, in one aspect, it is provided a biocompatible implant comprising one or more metal(s), metal alloy(s), and/or metal oxide(s) wherein a compound selected from the group consisting of an IP, an ester of an IP, and/or a pharmaceutically acceptable salt thereof or a combination thereof, is covalently bound to at least a part of a metal, metal alloy or metal oxide surface of said biocompatible implant. The invention also comprises a biocompatible implant comprising titanium, a titanium alloy and/or titanium oxide, wherein a compound selected from the group consisting of an IP, an ester of an IP, and/or a pharmaceutically acceptable salt thereof, or a combination thereof, is covalently bound to at least a part of said titanium, titanium alloy or titanium oxide surface of said biocompatible implant.

Figure 4:
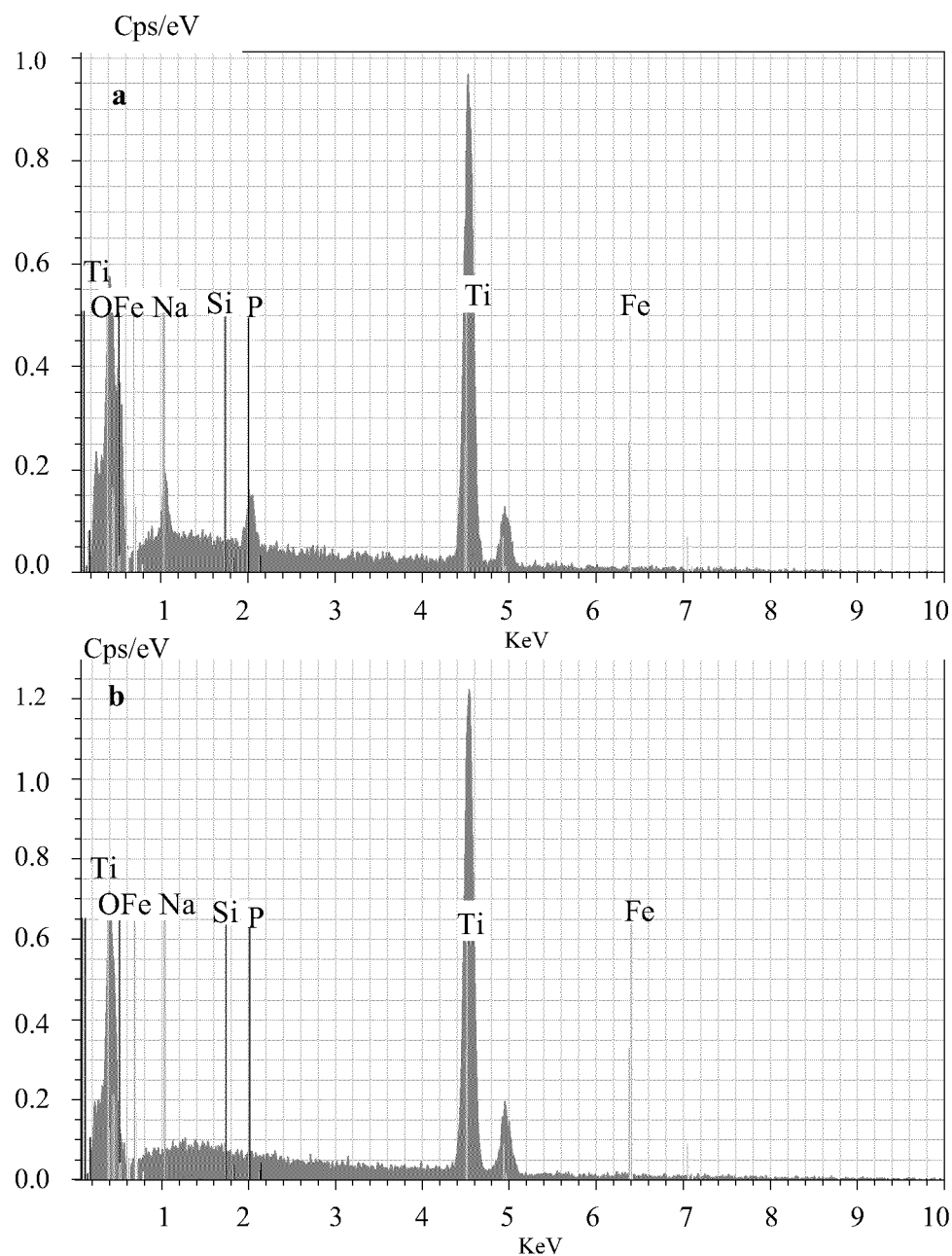
FIG. 4. Characterization of Ti surfaces after IP6 physical adsorption (a) EDS analysis of samples non rinsed, (b) EDS analysis of rinsed samples.

Previously, inositol hexaphosphate has been used for implants, but the binding methods were mainly focused on physic-chemical absorption, which are labile interactions. These can easily be removed just by rinsing (see e.g. FIG. 4). These obstacles have now been overcome by the present inventors, which have successfully produced an implant comprising covalently bound IP.

The covalent bond is effected between a metal, metal alloy and/or metal oxide surface of an implant according to the invention, such as a titanium, titanium alloy or titanium oxide implant surface, and an IP, an ester of an IP, and/or a pharmaceutically acceptable salt thereof, or a combination thereof. Such a covalent bond can e.g. be effected by using a linker, such as a silicon linker, such as APTES ((3-aminopropyl) triethoxysilane), by said linker being positioned between the metal, metal alloy or metal oxide surface and the IP, ester of an IP, and/or a pharmaceutically acceptable salt thereof, or combination thereof, thereby forming a three-part-complex between said metal, metal alloy and/or metal oxide, linker and the IP (see FIG. 2).

Accordingly, said IP, ester or pharmaceutically acceptable salt thereof and optionally said linker, may thereafter form a covalent coating on a metal, metal alloy or metal oxide surface of the biocompatible implant. Hence, it is also herein disclosed a biocompatible implant comprising one or more metal(s), metal alloy(s), and/or metal oxide(s) wherein at least a part of a metal, metal alloy or metal oxide surface of said biocompatible implant comprises a coating of a compound selected from the group consisting of an IP, an ester of an IP, and/or a pharmaceutically acceptable salt thereof or combination thereof, and a linker, such as a silicon linker, such as (3-aminopropyl) triethoxysilane (APTES).

Organic phosphate groups (e.g. from oligonucleotides) can also be conjugated to primary amines using N-(3-dimethylaminopropyl)-N'-ethylcarbodiimide (EDC) as a cross-linker. Therefore. IP can be derived through phosphate groups by conjugation to primary amines via a reactive phosphorylimidazolide intermediate, which may promote the covalent binding to the aminosiloxane titanium surface.

To covalently link a compound to a metal, metal alloy or metal oxide surface, a highly energetic UV light that generates reactive groups on Ti, and as well reactive binding sites within the molecules that are to be coated to the surface in just one step, may be used (Petzold, Lyngstadaas et al. 2008). Highly energetic UV light affects binding states between atoms in molecules. In ambient environment, energy is transferred to molecules which then react further with oxygen molecules, which themselves are highly susceptible to excitation. This process is called photooxidation. $TiO_2$ is a well-known photocatalyst (Nakamura. Sirghi et al.

2002; Wu, Wang et al. 2006); electron-hole pairs are generated, reactive oxygen compounds are released, and water molecules dissociate and adsorb at the surface if irradiated with UV light (Mills and LeHunte 1997; Wang, Hashimoto et al. 1998; Miyauchi, Kieda et al. 2002). At the same time, biomolecules are oxidized by UV light increasing their reactivity and allowing the formation of covalent bonds with the photooxidized $TiO_2$ surface.

An "implant" as referred to herein can be described as a synthetic or natural material used to replace a part of a living system or to function in intimate contact with living tissue. Hence, a "biocompatible implant" can be described as an implant which does not cause any significant adverse bodily reactions when introduced into a mammalian body, such as any significant reaction of the immune system. Accordingly, said implant is constructed to interact with the mammalian body and to facilitate its introduction.

The term "osseointegration" as mentioned herein, refers to a characteristic of an implant according to the invention which refers to the direct structural and functional connection between living bone and the surface of said implant without growth of fibrous tissue at or on the bone-implant interface. It is not enough to improve bone growth in the vicinity of the implant, if a direct connection between the implant and the new bone does not exist. Thus, it is possible to improve bone growth without modulating osseointegrative properties of the implant, which will not result in a strong bone-implant interface that resists mechanical disruption, but will lead to soft tissue formation at the interface instead of bone due to an interfacial implant movement. The biocompatible implant of the present invention allows the modulation of the osseointegration. This implies the advantage that certain implants may be temporary and therefore it is not desirable that the implant be connected with the bone, while others may be permanent, for which an improved osseointegration will be sought.

As an example, an implant is "osseointegrated" if the bone-implant interface has several characteristics: (1) good mechanical stability studied by biomechanical tests like pull-out, (2) absence of inflammatory reaction and tissue necrosis, (3) a peri-implant bone that has a highly mineralized bone matrix, characterized by micro-computed analysis, and is low in protein, (4) the colonization of the implant surface by cells of the osteoblastic lineage, based on gene expression of several molecular markers.

A "covalent" bond is a form of chemical bond that is characterized by the sharing of pairs of electrons between atoms, as compared to ionic bonds where the atoms are bound together by the attraction between oppositely-charged ions. The strength of a covalent bond depends on the angular relation between atoms in polyatomic molecules. The present invention is primarily focused, but not restricted to, single covalent bonds between oxygen atoms from the oxidised surface of the metal and the active biomolecule and/or single covalent bonds between oxygen atoms from the oxidised surface of the metal and a linker in addition to single covalent bones between the linker and the active biomolecule. The hybridation of the central atom of the bond may be sp3 (definition based on the valence bond theory. The energy of the covalent bonds can typically be higher than about 30 kJ/mol, preferably higher than about 100 kJ/mol, more preferably higher than about 150 kJ/mol.

In the present context, the phrase "implant" includes within its scope any device intended to be implanted into the body of a vertebrate animal, in particular a mammal, such as a human. Non-limiting examples of such devices are medical devices that replace anatomy or restore a function of the body such as the femoral hip joint; the femoral head; acetabuiar cup; vascular stents, elbow including stems, wedges, articular inserts; knee, including the femoral and tibial components, stem, wedges, articular inserts or patellar components; shoulders including stem and head; wrist; ankles; hand; fingers; toes; vertebrae: spinal discs; artificial joints; dental implants; ossiculoplastic implants; middle ear implants including incus, malleus, stages, incus-stapes, malleus-incus, malleus-incus-stapes; cochlear implants; orthopaedic fixation devices such as nails, screws, staples and plates; heart valves; pacemakers; catheters; vessels; space filling implants; implants for retention of hearing aids; implants for external fixation; prosthetic discs for spinal fixation and also intrauterine devices (IUDs), as well as bioelectronic devices such as intracochlear or intracranial electronic devices. Included are also surgical implants.

Medical implants may also be denoted as medical prosthetic devices or implants. Generally, a medical implant is composed of one or several implant parts. Accordingly, the present invention also relates to one or more biocompatible implant components or parts comprising one or more metal(s), metal alloy(s), and/or metal oxide(s).

In the present context, the term "orthopedic implant" includes within its scope any device intended to be implanted into the body of a vertebrate animal, in particular a mammal such as a human, for preservation and restoration of the function of the musculoskeletal system, particularly joints and bones, including the alleviation of pain in these structures. Within this context are also envisaged orthopedic fixation devices and orthopedic joint replacements.

In the present context, the term "dental implant" includes within its scope any device intended to be implanted into the oral cavity of a vertebrate animal, in particular a mammal such as a human, in tooth restoration procedures. Dental implants may also be denoted as dental prosthetic devices. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation may alone be referred to as an implant even if other parts are to be connected thereto.

In the context of the present invention, the terms "implant", "medical implant", "graft material", "device" and "medical device" may be used interchangeably herein. It should be understood that in all aspects of the present invention, whenever a "biocompatible implant" or an "implant" is referred to herein this includes any of the implants mentioned herein and/or which is known to the skilled person to be suitable for the present purpose.

Bone is a multifunctional organ that consists of a structural framework of mineralized matrix and contains heterogeneous populations of chondrocytes, osteoblasts, osteocytes, osteoclasts, endothelial cells, monocytes, macrophages, lymphocytes and hemopoietic cells. Bone growth is regulated by complex interactions between different intercellular and extracellular players. In general, mineralized tissue is vital to many characteristic adaptive phenotypes in vertebrates. Hard and/or mineralized tissue describes a variety of different naturally occurring tissue types that have become mineralized, and/or tissue having a firm intercellular substance.

When a biocompatible implant comprising one or more metal(s), metal alloy(s), and/or metal oxide(s) is referred to, this can also refer to an implant which comprises one or more additional biocompatible material(s), such as synthetic or plastic material(s). Alternatively, a biocompatible implant can also consist almost entirely, or fully, of a metal, metal alloy and/or metal oxide, such as titanium, a titanium alloy and/or a titanium oxide. In some aspect, said implant may have a surface of a metal, metal alloy and/or metal oxide, and the core may comprise other suitable materials for the present purpose. The metal, metal alloy and/or metal oxide surface may be added on to an implant when the implant per se is made from another material or when the implant is partly made of metal, metal alloy and/or metal oxide. This is all referred to as an implant comprising a metal, metal alloy and/or metal oxide.

Said biocompatible implant may also comprise more than one metal, metal alloy and/or metal oxide, such as for example titanium, a titanium alloy and/or a titanium oxide, in combination with other metal(s), metal alloy(s) and/or metal oxide(s), such as zirconium, an alloy and/or an oxide thereof, tantalum, an alloy and/or an oxide thereof, hafnium, an alloy, and/or an oxide thereof, niobium, an alloy and/or an oxide thereof, chromium-vanadium alloy end/or a combined oxide and stainless steel. Said implant can also be a graft material, preferably a metal oxide scaffold comprising titanium oxide.

In some aspects of the invention, the biocompatible implant according to the invention can be exposed to UV radiation prior, simultaneously and/or after coating with an IP. For example $TiO_2$ is a well-known photocatalyst (Nakamura, Sirghi et al. 2002). If the surface is irradiated with UV light, electron-hole pairs are generated, reactive oxygen compounds are released, and water molecules dissociate and adsorb at the surface. Those hydroxide groups cause an increased hydrophilicity of the surface.

It should be understood that whenever IP is mentioned in the context of any aspect or embodiment of the invention, this comprises inositol phosphate, an ester of an IP, and/or a pharmaceutically acceptable salt thereof, or a combination thereof, in such a context, even if not explicitly referred to, and even if only IP is referred to.

Said IP can comprise 1, 2, 3, 4, 5 or 6 phosphate groups. An example of an IP, is an IP which comprises 6 phosphate groups, herein also interchangeably referred to as phytate. IP6 or IP6, (Myo-inositol-1,2,3,4,5,6-hexakisphosphate, see FIG. 2).

Whenever a linker is mentioned in the context of the present invention, this refers to a chemical entity that is used for binding said IP, an ester of an IP, and/or a pharmaceutically acceptable salt thereof, or combination thereof, to the metal, metal alloy or metal oxide surface, of the biocompatible implant, thereby forming a covalent bond between the phytate and the metal, metal alloy and/or metal oxide. One part of the linker reacts with, and thereby binds to, the metal, metal alloy or metal oxide surface. Another part of the linker reacts with and binds to said IP, ester of an IP, and/or pharmaceutically acceptable salt thereof, or combination thereof, thereby forming a covalent bond between said IP and said metal, metal alloy or metal oxide surface. This may provide for a surface of said biocompatible implant which is a particularly active modulator, preferably improver, of osseointegration. Examples of linkers that may be used in the context of the present invention are linkers selected from the group consisting of anhydrides, alcohols, acids, amines, epoxies, isocyanates, silanes, halogenated groups, and polymerizable groups. The linker selected from the group of silanes, may be (3-aminopropyl) triethoxysilane (APTES).

As mentioned herein, a biocompatible implant comprising one or more metal(s), metal alloy(s) and/or metal oxide(s), has to at least a part of a metal, metal alloy or metal oxide surface of said biocompatible implant a compound selected from the group consisting of an IP, an ester of an IP, and/or a pharmaceutically acceptable salt thereof, or a combination thereof, covalently bound thereto. Furthermore, this can also be referred to as the implant having a coating of covalently bound IP on a metal, metal alloy or metal oxide surface.

Also encompassed by the present invention is a biocompatible implant comprising one or more metal(s), metal alloy(s) and/or metal oxide(s), wherein to at least a part of a metal, metal alloy or metal oxide surface of said biocompatible implant a combination of IPs are covalently bound, said combination comprising IP6 and at least one of the other lower IPs, such as inositol triphosphate to inositol pentaphosphate (IP3 to IP5), such as IP5.

Examples of esters of IPs which are encompassed by the invention are $C_1$-$C_{20}$ alkyl esters, such as $C_1$-$C_{10}$ alkyl esters, such as $C_1$-$C_6$ alkyl esters, such as $C_1$, $C_2$, $C_3$, $C_4$, $C_5$, $C_6$, $C_7$, $C_8$, $C_9$, or $C_{10}$ alkyl esters.

When "at least a part of a metal, metal alloy or metal oxide surface" is referred to this means that a metal, metal alloy, metal oxide or a combination thereof surface of an implant need not be fully covered by covalently bound IP, but some parts of the metal, metal alloy and/or metal oxide surface may lack an IP coating, contain less IP and/or some parts of the metal, metal alloy and/or metal oxide surface may also comprise physically bound IP in addition to the covalently bound IP, e.g if remaining after the treatment of the surface to attach the IP thereto. Furthermore, some parts of the surface of the implant according to the invention need not comprise a metal, metal alloy and/or metal oxide, but may instead comprise other materials, or combinations thereof.

Disclosed herein is a biocompatible implant, wherein to a metal, metal alloy or metal oxide surface thereof, covalently bound IP, ester of an IP, and/or a pharmaceutically acceptable salt thereof, or combination thereof, comprises at least about 50% of weight of the total weight of IP, ester of IP, pharmaceutically acceptable salt thereof, or combination thereof, present on said metal, metal alloy or metal oxide surface. In other aspects, at least about 60, 65, 70, 75, 80, 85, 90, 95 or 99% of weight of the total weight of IP is covalently bound to a metal, metal alloy or metal oxide surface of said implant.

A coating comprising covalently bound IP compounds can further comprise other active biomolecules on the metal, metal alloy or metal oxide surface of the implant, such as, but not limited to natural biomolecules (i.e. naturally occurring molecules derived from natural sources), synthetic biomolecules (i.e. naturally occurring biomolecules that are synthetically prepared and non-naturally occurring molecules or forms of molecules prepared synthetically) or recombinant biomolecules (prepared through the use of recombinant techniques). Examples of biomolecules of interest include, but are not limited to biomolecules, such as bioadhesives, cell attachment factors, biopolymers, blood proteins, enzymes, extracellular matrix proteins and biomolecules, growth factors and hormones, nucleic acids (DNA and RNA), receptors, synthetic biomolecules, vitamins, drugs such as biphosphonates, biologically active ions such as fluoride, marker biomolecules etc.

When said IP, ester of an IP, pharmaceutically acceptable salt thereof, or combination thereof, is covalently bound to a metal, metal alloy or metal oxide surface of said biocompatible implant, this also refers to a biocompatible implant comprising a coating of covalently bound IP, and optionally a linker such as APTES. Hence, in this context, the terms coating, coated, bound to, cover, covered, can be interchangeably used herein in the context of describing the surface of the implant.

Figure 1A:
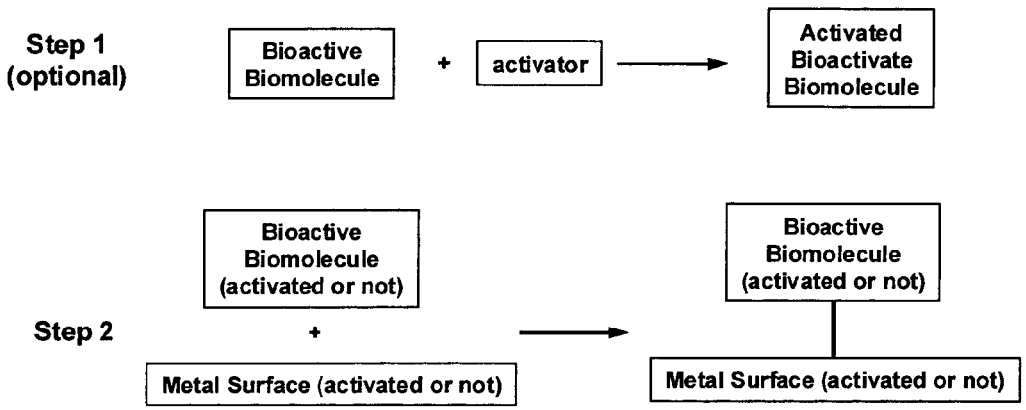
FIG. 1: Schematic picture describing the addition of a biomolecule onto a metal surface without (a) or with a linker (b).
Figure 1B:
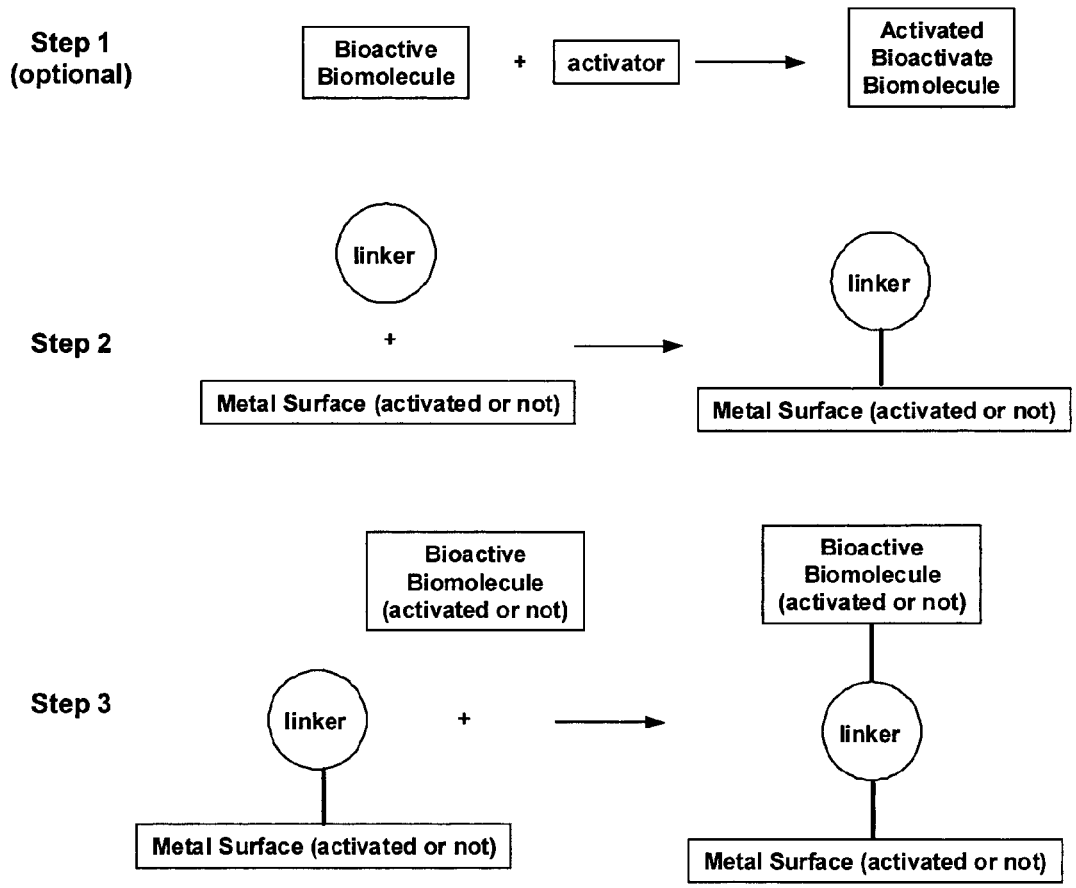
Figure 2:
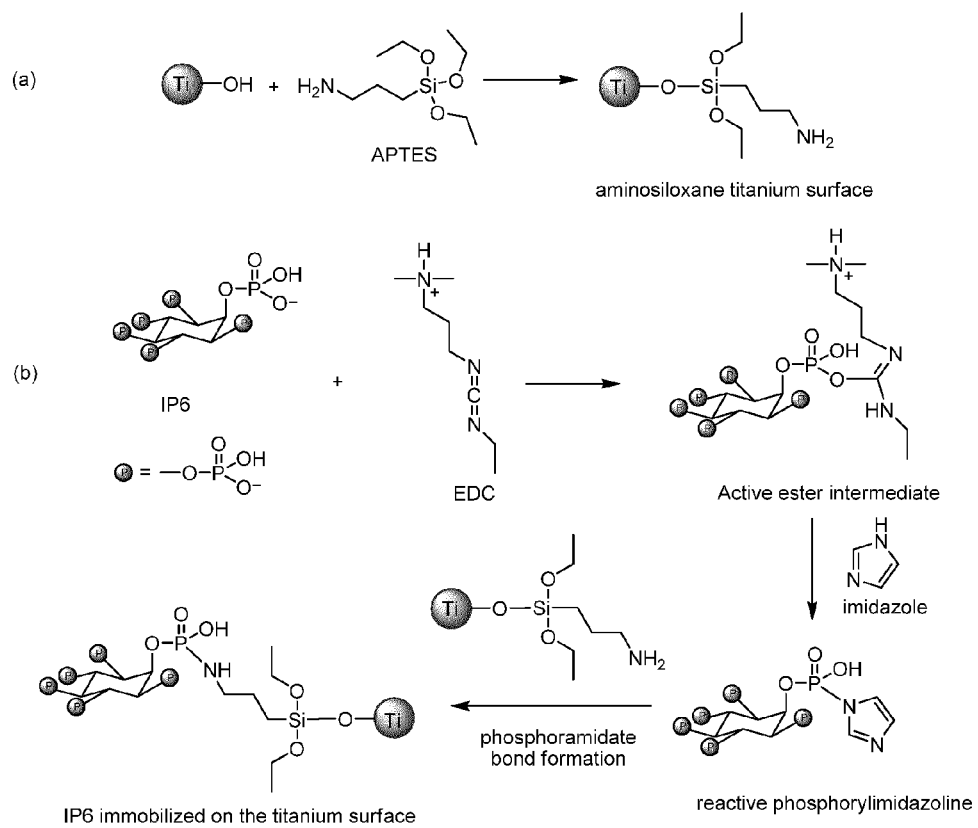
FIG. 2. (a) Reaction of $TiO_2$ surface with APTES. (b) Activation of IP6 using the carbodiimide crosslinker EDC and imidazole, and subsequent attachment of the biomolecule to the titanium surface (note: only showing activation of one phosphate group).

Herein, a covalent bond of the IP, an ester of an IP, a pharmaceutically acceptable salt thereof, or a combination thereof, to a metal, metal alloy or metal oxide surface can be effected through at least one linker. Said linker can hence in one part thereof be bound to a metal, metal alloy or metal oxide surface, by performing a chemical reaction between that part of said linker and said metal, metal alloy or metal oxide surface. The linker can in another part thereof be attached to said IP, an ester of an IP, and/or a pharmaceutically acceptable salt thereof, or a combination thereof, by performing a chemical reaction between that part of said linker and the IP. Thereby, a covalent bond between a metal, metal alloy or metal oxide surface and said IP may be formed via said linker. Accordingly, when a linker is used in the context of the present invention, said linker may form a covalent bond between said IP and the metal surface. The binding of the linker to said IP and to the metal, metal alloy or metal oxide surface can be in any part of the linker which is suitable for the purpose, i.e. a part of the linker which is able to chemically react with the IP or the metal, metal alloy or metal oxide surface. Hence, a chemical reaction will occur between the respective parts of the linker, the IP and the metal, metal alloy or metal oxide surface by virtue of chemically reactive groups. An example of such an event is illustrated in FIGS. 1 and 2.

Said linker can be a linker which contains silicon, such as 3-aminopropyltriethoxysilane (APTES). Such a linker can also be referred to as being chosen from the group of silanes. Such a linker is applicable to all aspects of the invention. Hence, the present invention also relates to a biocompatible implant, comprising one or more metal(s), metal alloy(s) and/or metal oxide(s), as exemplified herein, wherein said metal, metal alloy and/or metal oxide is present on a surface of said biocompatible implant, and wherein a linker and an IP, an ester of an IP, a pharmaceutically acceptable salt thereof, or a combination thereof, forms a coating on at least a part of a metal, metal alloy or metal oxide surface of said biocompatible implant, said coating comprising an IP, an ester of an IP, a pharmaceutically acceptable salt thereof or a combination thereof, which is mainly covalently bound to said metal, metal alloy or metal oxide surface.

In all aspects of the invention, a metal, metal alloy and/or metal oxide can be selected from the group consisting of titanium, an alloy and/or and oxide thereof, zirconium, an alloy, and/or an oxide thereof, tantalum, an alloy and/or and oxide thereof, hafnium, an alloy, and/or and oxide thereof, niobium, an alloy, and/or an oxide thereof, chromium-vanadium alloy and/or a combined oxide and stainless steel. According to the present invention, such a metal can be titanium, a titanium alloy and/or a titanium oxide. Said implant can also be a graft material, preferably a metal oxide scaffold comprising titanium oxide.

As previously mentioned herein, a biocompatible implant can be a surgical implant, an orthopedic implant, a dental implant or an orthopedic fixation device. A biocompatible implant according to the invention can also be a device selected from an orthopedic joint replacement or a prosthetic disc for spinal fixation.

The present invention also relates to a method for producing a biocompatible implant comprising one or more metal(s), metal alloy(s), and/or metal oxide(s) as exemplified herein, such as titanium, a titanium alloy and/or a titanium oxide, wherein to at least a part of a metal, metal alloy and/or metal oxide surface of said biocompatible implant a compound selected from the group consisting of an IP, an ester of an IP, and/or a pharmaceutically acceptable salt thereof, or a combination thereof, is covalently bound. A method comprises adding and reacting an IP, an ester of an IP, a pharmaceutically acceptable salt thereof, or a combination thereof, to/with a metal, metal alloy and/or metal oxide surface of said biocompatible implant.

A method for producing a biocompatible implant can further comprise a step of chemically pre-treating a metal, metal alloy or metal oxide surface of a biocompatible implant before contacting and/or reacting an IP, an ester of an IP, and/or a pharmaceutically acceptable salt thereof, or combination thereof, therewith. Thereafter, when added, at least a part of the IP, ester of an IP, pharmaceutically acceptable salt thereof, or combination thereof, forms a covalent bond to a metal, metal alloy or metal oxide surface of said implant. A method also comprises a step of contacting, reacting and binding a linker to a chemically pre-treated metal, metal alloy or metal oxide surface before contacting the IP with the metal, metal alloy or metal oxide surface. Thereafter, the IP is put in contact with the metal, metal alloy or metal oxide surface to which the linker has already bound, to react therewith. By using such an alternative, a covalent bond may be effected between the IP and said metal, metal alloy or metal oxide surface via a linker. Hence, when a linker is used the covalent bond can also be established via a linker. However, the invention is not limited thereto but also encompasses an IP which has formed a covalent bond directly with the metal, metal alloy or metal oxide surface of an implant. The above mentioned steps of attaching a linker and an IP to a metal, metal alloy or metal oxide surface may also be performed in an alternate order.

As mentioned herein, said linker can comprise silicon, and said linker comprising silicon can be 3-aminopropyltriethoxysilane (APTES), which is used in a method as disclosed herein. A method can also comprise a washing step after the addition of the IP, ester of an IP, pharmaceutically acceptable salt thereof, or combination thereof, to said chemically pre-treated surface of said implant. As mentioned herein, a biocompatible implant used in a method herein can comprise a metal, metal alloy and/or metal oxide selected from the group consisting of titanium, an alloy and/or an oxide thereof, zirconium, an alloy and/or an oxide thereof, tantalum, an alloy and/or an oxide thereof, hafnium, an alloy and/or an oxide thereof, niobium, an alloy and/or an oxide thereof, chromium-vanadium alloy and/or a combined oxide and stainless steel.

A pre-treatment according to the present invention, can e.g. be performed by passivation, piranha or by the treatment with one or more alkali solution(s). Non-limiting examples of such pre-treatments are further described in the experimental section. Furthermore, in a separate step of a method, the IP, ester of an IP, pharmaceutically acceptable salt thereof, or combinations thereof is/are activated as described herein before being added to an optionally chemically pre-treated metal, metal alloy or metal oxide surface of said biocompatible implant.

Such activation can be performed by adding a carbodiimide cross-linker, such as N-(3-dimethylaminopropyl)-N'-ethylcarbodiimide (EDC) to said IP, ester of an IP, pharmaceutically acceptable salt thereof, or combination thereof. Such activation can also comprise the formation of a phosphoramidate during said activation.

The formation of a phosphoramidate, which is further illustrated in FIG. 2, comprises the steps of adding 1-ethyl-3-3-dimethiylaminopropylcarbodiimide hydrochloride to the IP, for the formation of an active ester, and thereafter adding imidazole for the formation of an active phosphoramidate. The active phosphoramidate comprising the IP is thereafter added to a metal, metal alloy or metal oxide surface of the implant.

Accordingly, the present invention also relates to a method comprising the formation of a phosphoramidate, which comprises the steps of adding 1-ethyl-3-3-dimethylaminopropylcarbodimide hydrochloride to said IP, ester of an IP, pharmaceutically acceptable salt thereof, or combination thereof, for the formation of an active ester, and thereafter adding imidazole to said active ester for the formation of an active phosphoramidate. It should be noted that the objective of this reaction is to generate an IP according to the invention with an appropriate leaving group, hence other suitable reactants may also be used for performing such a reaction.

Hence, described herein is a method where a linker, such as APTES, is firstly reacted with a chemically pre-treated metal, metal alloy or metal oxide surface of an implant, and wherein the IP is activated and subsequently reacted with the linker bound to the metal, metal alloy or metal oxide surface to form a stable covalent bond between the metal, to metal alloy or metal oxide surface and the IP.

The present invention also relates to a biocompatible implant which is obtainable through any method as described herein.

In other aspects, the present invention also relates to a method for introducing a biocompatible implant as defined herein into a patient in need thereof, said method comprising the steps of providing a biocompatible implant comprising one or more metal(s), metal alloy(s) and/or metal oxide(s), wherein to at least a part of a metal, metal alloy or metal oxide surface of said biocompatible implant a compound selected from the group consisting of an IP, an ester of an IP, and/or a pharmaceutically acceptable salt thereof and/or a combination thereof is covalently bound and thereafter introducing said implant into said patient by a surgical procedure. An implant of the invention may be introduced into a patient who needs a replacement of a body part, such as a hip or a knee, and where modulation, preferably improvement, of osseointegration properties is needed.

The present invention also relates to the use of a biocompatible implant comprising one or more metal(s), metal alloy(s) and/or metal oxide(s), wherein a compound selected from the group consisting of an IP, an ester of an IP, and/or a pharmaceutically acceptable salt thereof and/or a combination thereof is/are covalently bound to at least a part of a metal, metal alloy or metal oxide surface of said biocompatible implant, in the modulation, preferably improvement, of osseointegration. The present invention also relates to the use of an IP, an ester of an IP, and/or a pharmaceutically acceptable salt thereof, or a combination thereof, which is covalently bound to a metal, metal alloy or metal oxide surface, in the modulation, preferably improvement, of osseointegration.

In another aspect, it is herein described a biocompatible implant comprising one or more metal(s), metal alloy(s) and/or metal oxide(s), wherein a compound selected from the group consisting of an IP, an ester of an IP, and/or a pharmaceutically acceptable salt thereof, or a combination thereof, is/are covalently bound to at least a part of a metal, metal alloy or metal oxide surface of said biocompatible implant, for use in the modulation, preferably improvement, of osseointegration, and wherein the osseointegrative effect is achieved by virtue of the combination of the covalently bound IP to the metal, metal alloy or metal oxide surface, said covalent bond optionally being effected through at least one linker, such as APTES. In accordance therewith, the present invention is also related to the use of a biocompatible implant comprising one or more metal(s), metal alloy(s) and/or metal oxide(s), wherein a compound selected from the group consisting of an IP, an ester of an IP, and/or a pharmaceutically acceptable salt thereof, or a combination thereof, is/are covalently bound to at least a part of a metal, metal alloy or metal oxide surface of said biocompatible implant, in the manufacture of a medical device for use in the modulation, preferably improvement, of osseointegration.

The invention is further illustrated by the following, non-limiting examples.

EXPERIMENTAL SECTION

Abbreviations and Acronyms
  ALP: Alkaline phosphatase
  APTES: (3-aminopropyl) triethoxysilane
  ΔH: Enthalpy
  BrdU: Bromodeoxyuridine
  CalcR: Calcitonin receptor
  Car2: Carbonic anhydrase type II
  CEIC-IB: Ethical Committee of Balearic Islands
  CFMS: Colony stimulating factor receptor
  Col1A: type 1 collagen
  CtsK: Cathepsin K
  DMEM: Dulbecco modified Eagles medium
  DMEM-LG: Dubeloco's modified Eagle's medium with low glucose and Glutamax
  EDC: N-(3-dimethylaminopropyl)-N'-ethylcarbodiimide
  EDS: Energy-dispersive X-ray spectroscopy
  FBS: Foetal bovine serum
  GAPDH: Glyceraldehyde-3-phosphate dehydrogenase
  H+-ATPase: Vacuolar-type H+ ATPase
  hUC-MSC: Human umbilical cord derived mesenquimal stem cells
  ICP-AES: Plasma atomic emission spectrometer
  IP6: Myo-inositol-1,2,3,4,5,6-hexakisphosphate, phytic acid, phytate
  LDH: Lactate dehydrogenase
  MMP-9: Metalloproteinase-9
  OC: osteocalcin
  OCLs: Osteoclasts
  PCR: Polymerase chain reaction
  pNPP: p-Nitrophenyl Phosphate
  RANKL: Receptor activator of NF-κB ligand
  rRNA: Ribosomal RNA
  Runx2: Runt-related transcription factor 2
  SEM: Scanning electronic microscopy
  Ti: Titanium
  TRAP: Tartrate resistant acid phosphatase
  UV: Ultra-violet
Experimental Reagents APTES, Toluene, EDC, Imidazole, Sulfuric acid, Isopropyl alcohol, Acetone. Ethanol, Sodium Hydroxide, the TRAP-staining kit, FITC-phalloidin. Fluoroshield with DAPI, ascorbic acid, β-glycerophosphate, hydrocortisone collagenase type IA and p-Nitrophenyl Phosphate were provided by Sigma-Aldrich (St. Louis, Mo., USA). TiO2 powder (Kronos 1171) was obtained from Kronos Titan GmbH (Leverkusen, Germany). The transformed murine monocytic cell line RAW 264.7 was obtained from ATCC (Manassas, Va., USA). The mouse osteoblastic cell line MC3T3-E1 was obtained from DSMZ (Braunschweig, Germany). DMEM, Fetal bovine serum, penicillin and streptomycin were obtained from PAA Laboratories GmbH (Pasching, Austria). α-Minimum essential media and DMEM-LG were obtained from GIBCO (Grand Island, N.Y., US). FBS was purchased to HyClone (Thermo Scientific, Logan, USA) Cytotoxicity Detection Kit (LDH), the Cell Proliferation ELISA kit, Tripure reagent, Lightcycler-FastStart DNA MasterPLUS SYBR Green I, Midazolam (Dormicum®) were obtained from Roche Diagnostics (Mannheim, Germany). RANKL was obtained from PeproTech (Rocky Hill, N.J., USA). The High Capacity RNA to cDNA kit was obtained from Applied Biosystems Life Technologies (Carlsbad, Calif., USA). Dentine slices were purchased at Immunodiagnostic Systems (Boldon, UK), Alkaline phosphatase was obtained from Promega (Madison, US). BCA protein assay kit was purchased from Pierce (Rockford, Ill., USA). Lidocain/adrenalin (Xylocain/Adrenalin®) was purchased from AstraTech AB (Molndal, Sweden). Chlorhexidingluconat (Klorhexidin) was provided by Galderma (Nordic AB, Sweden). Buprenorphin (Temgesic®) was obtained from Reckitt & Colman (Hull, UK). Fluanison/fentanyl (Hypnorm®) was purchased from Janssen Pharmaceutica (Beerse, Belgium). Pentobarbital (Mebumale®) was provided by Rikshospitalets Apotek (Oslo, Norway).

Other routine chemicals were provided by Panreac (Barcelona, Spain) and Sigma-Aldrich (St. Louis, Mo., USA).

Example 1

Covalent Binding of Phytic Acid to Titanium Implants Using a Linker

IP6 was covalently bound on Ti disks by the use of a silicon linker. In particular, hydroxyl groups of the TiO2 surface reacted with the alkoxy groups on APTES forming a covalent —Si—O—Si— bond, resulting in immobilization of the aminosiloxane moiety on the TiO2 surface. On the other hand, it was hypothesized that derivatization of IP6 phosphate groups using the carbodiimide crosslinker EDC and imidazole would promote the covalent binding to the aminosiloxane titanium surface (see FIG. 2).
Materials and Methods
1. Silanization Ti coins were silanized in toluene solution of 10% APTES at RT for 24 hours, and dried under vacuum overnight.
2. Covalent Binding of IP6

Silanizated Ti coins were immersed in an aqueous solution of EDC and IP6. 3 mL of imidazole solution 6000 mg/L were added immediately and the mixture was sonicated at room temperature. Non-reacted EDC, IP6 and by-products were removed washing gently with water. Finally. Ti coins were dried under vacuum overnight.
3. Characterization of the Modified Surfaces by Scanning Electronic Microscopy and Energy-Dispersive X-Ray Spectroscopy.

Figure 3:
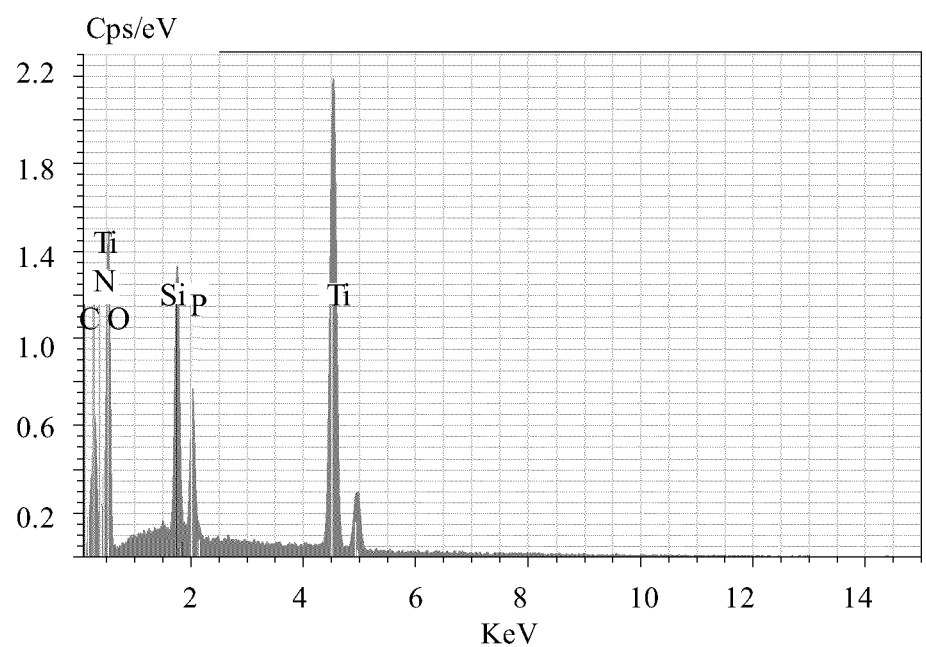
FIG. 3. EDS analysis of Ti surfaces after IP6 covalent binding using a linker.

A scanning electronic microscope (SEM) HITACHI S-3400N was used to study the surface of modified Ti coins. Microanalysis system R-X EDS, Bruker AXS XFlash 4010 was used for the qualitative and semi quantitative analysis.
4. Immobilized Phosphorus Quantification Surface modified Ti coins were treated with nitric acid 2N and heated for 30 min at 50° C. Phosphorous total content was determined by inductively coupled plasma atomic emission spectroscopy (ICP-AES) with Perkin-Elmer Optima 5300 spectrometer.
Results Modified Ti coins were analysed by SEM-EDS and ICP-AES confirming that Si and P peaks were detected on the Ti surface (FIG. 3). Moreover, after release testing of modified Ti coins P was detected in solution, consistent with the fact that IP6 was attached to the Ti surface. The correlation of the P signal with IP6 quantities deposited on the Ti coin indicated an amount of linked IP6 of 1.64 µg/Ti coin.

Example 2

Physical Adsorption Vs Covalent Binding of Phytic Acid to Titanium Implants

As an alternative method for covalent binding. IP6 can also be physically adsorbed onto a titanium surface. Negatively charged phosphate groups contained in the IP6 molecule show a strong affinity for metal oxide surfaces and can therefore directly interact with the titanium surface. This attachment (called physisorption) is achieved through intermolecular forces of low binding energy ($\Delta H<50$ kJ mol-1), i.e. van der Waals forces. Due to the low binding forces this type of adsorption is reversible simply by washing, being the medical device useless for modulation of osseointegration properties. In this example, we compared coating of IP6 to Ti surfaces by physical adsorption versus covalent binding.
Materials and Methods
1. Physical Adsorption Ti coins were rinsed with autoclaved water and washed with ethanol followed by ultrasonication of coins in autoclaved water for 5 min. and rinsed with pure water. IP6 solution (at concentrations of 0.1 mg/ml and 1 mg/ml in 70% ethanol) was sterilized by filtration. 10 µl of respective solution of IP6 were given on the surface of the coins and incubated for 24 h at 37° C.
2. Covalent Binding The experimental procedure developed in example 1 was used.
3. Characterization of the Modified Surfaces by Scanning Electronic Microscopy and Energy-Dispersive X-Ray Spectroscopy.

The experimental procedure developed in example 1 was used.
4. Immobilized Phosphorus Quantification The experimental procedure developed in example 1 was used.
Results After physical adsorption, one part of the samples was rinsed with autoclaved water to remove unbound IP6 and the other part was directly analyzed by SEM-EDS and ICP-AES, EDS analysis showed Na and P peaks on the Ti surface after physical adsorption without rinse (FIG. 4a). However, these signals disappeared when samples were rinsed with autoclaved water (FIG. 4b). EDS results were confirmed by ICP-AES analysis observations (data not shown).

It was demonstrated that physical adsorption of IP6 to Ti surfaces results in a very weak interaction, since almost all IP6 is removed only by rinsing the coins in water for 5 seconds. Therefore, direct physical adsorption of IP6 on Ti coins is not a feasible process to bind this molecule to Ti coins and to prepare a bioactive coating.

Example 3

Chemical Pre-Treatment (Alkali, Passivation and Piranha) and Covalent Binding of Phytic Acid to Titanium Implants Using a Linker Covalent attachment of silicon compounds on Ti surfaces is based on the intrinsic ability of silanol groups to react with the hydroxyl groups present on the oxidized layer of an activated surface. For this purpose, various chemical pretreatments of Ti surface were examined (passivation, piranha and with alkali solution) to potentially increase the number of hydroxyl groups in the Ti surface to facilitate subsequent reaction with APTES. In consequence, it was hypothesized that increasing the number of aminosiloxane reactive groups would facilitate the covalent binding of IP6. After chemical pretreatment. Ti coins were subjected to the reaction conditions described in the experimental section of example 1 to immobilize IP6 using EDC as crosslinker.

Materials and Methods

1. Passivation Pretreatment

Ti coins were sonicated for 10 min in each of the following chemicals in succession: acetone (70% by volume), absolute ethanol, and water. Following sonication in water, the coins were placed in a 3:7 (v/v) nitric acid-water solution for 30 min at room temperature. Following this treatment, the samples were rinsed with water and placed in a covered water bath for 24 h. Finally. Ti coins were dried, packed and stored in 70% ethanol in dark at 4° C. until use.

2. Piranha Pretreatment

Ti coins were first sonicated for 30 min in 70% isopropyl alcohol. Following sonication, concentrated sulfuric acid was poured into a beaker and 35% hydrogen peroxide was slowly added to a final 7:3 (v/v) ratio of sulfuric acid to hydrogen peroxide and the resulting mixture was then gently mixed. Coins were immersed for 10 min in this solution before being removed and placed in a second, fresh, piranha solution (concentrated sulphuric acid/35% hydrogen peroxide 7:3 (v/v)), for 5 min. After this period, the Ti coins were rinsed twice with water before being placed in water bath for 24 h. Finally. Ti coins were dried, packed and stored in 70% ethanol in dark at 4° C. until use.

3. Alkali Pretreatment

Ti coins were ultrasonically cleaned in water, acetone, and ethanol for 20 min each, and finally in water for another 10 min. Subsequently, they were immersed in 5 M NaOH at 60° C. for 24 h. After the 24 h period, the substrate plates were gently washed with water. Finally, Ti coins were dried, packed and stored in 70% ethanol in dark at 4° C. until use.

4. Covalent Binding

The experimental procedure developed in example 1 was used.

5. Characterization of the Modified Surfaces by Scanning Electronic Microscopy and Energy-Dispersive X-Ray Spectroscopy.

The experimental procedure developed in example 1 was used.

6. Immobilized Phosphorus Quantification

The experimental procedure developed in example 1 was used.

Results

Different chemical pretreatments (passivation, piranha and with alkali solution) were examined to evaluate if increasing the number of hydroxyl groups present on the oxidized layer of the Ti surface would increase the amount of IP6 covalently bound to the surface. Not chemically pretreated surfaces were included in the experiment. The resulting modified Ti coins were analysed by SEM-EDS and ICP-AES.

Figure 5:
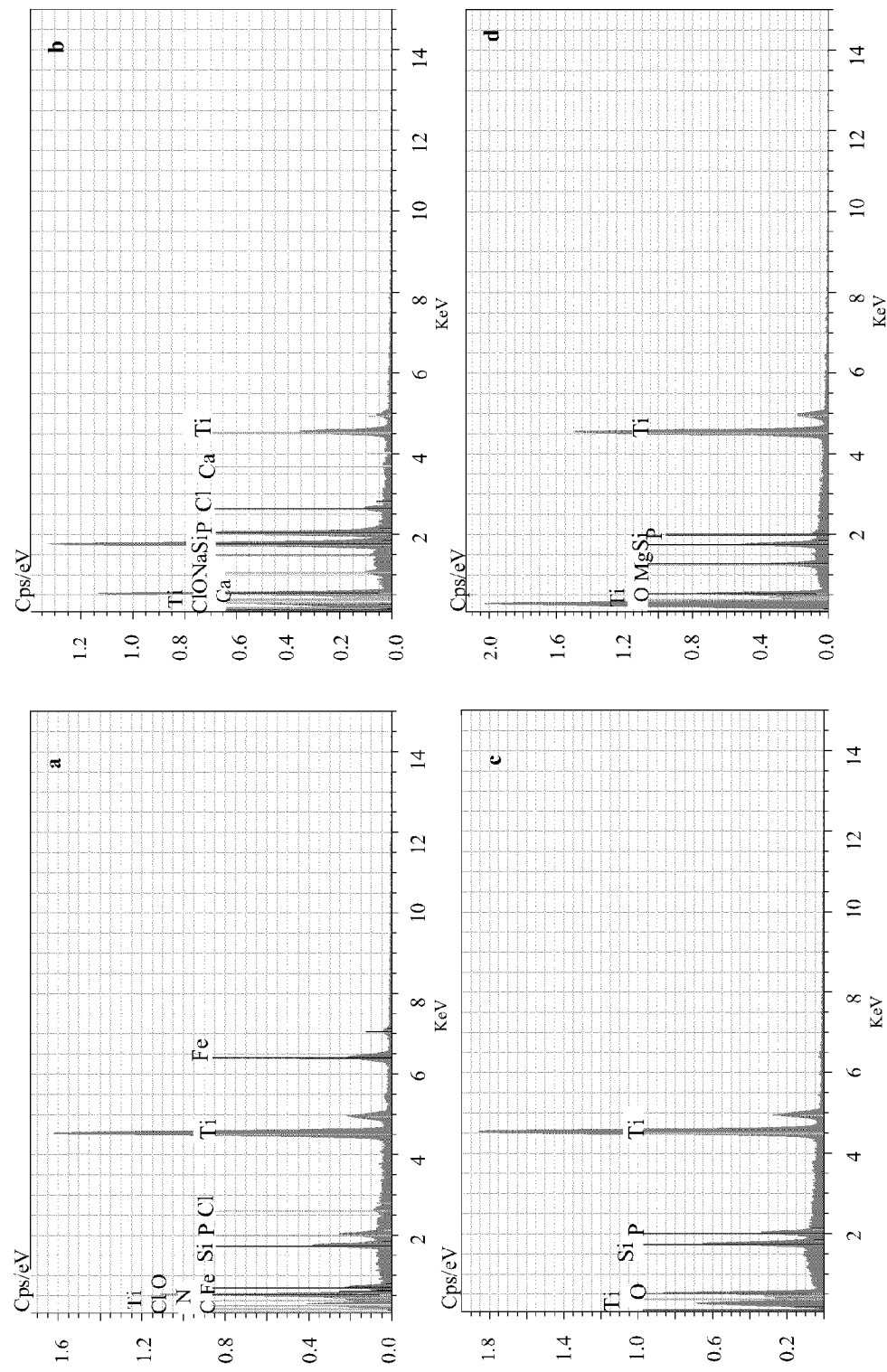
FIG. 5. EDS analysis of Ti surfaces after IP6 covalent binding using a linker (a) not chemically pretreated; (b) after passivation pretreatment; (c) after Piranha pretreatment; (d) after alkali pretreatment.

As shown by SEM-EDS analysis (FIG. 5), except for alkali pretreatment, the rest of modified Ti coins contained Si and P peaks indicating that immobilization of IP6 on the Ti surface was achieved.

Release testing of modified Ti coins and subsequent determination of total P content by ICP-AES confirmed prior observations by SEM-EDS. Passivation chemical pretreatment followed by IP6 immobilization allowed an increased deposition of IP6 (36.66 μg/Ti coin) compared to the other treatments.

Example 4

Covalent Binding of Phytic Acid to Ceramic Titanium Dioxide ($TiO_2$) Scaffolds Using a Linker The procedure developed in example 1 can be applied to $TiO_2$ scaffolds.

1. Preparation of $TiO_2$ Scaffolds

The scaffolds can be prepared by the polymer sponge methodology and using $TiO_2$ powder. The $TiO_2$ scaffolds can be sterilized prior the experiment by auto-claving them at 121° C. for 20 minutes.

2. Covalent Binding of IP6

The experimental procedure developed in example 1 can be used.

3. Characterization of the Modified Surfaces by Scanning Electronic Microscopy and Energy-Dispersive X-Ray Spectroscopy.

The experimental procedure developed in example 1 can be used.

4. Immobilized Phosphorus Quantification

The experimental procedure developed in example 1 can be used.

Results and Discussion Examples 1-4

With examples 1-4, it has been demonstrated that it has been possible to overcome the difficulties of permanently bind IP6 to an implant surface. Previously. IP6 has been used for implants, but the binding methods were mainly focused on physical-chemical absorption, which are labile interactions. These can easily be removed just by rinsing as we have shown in example 2, demonstrating the limited availability of IP6 after its physical absorption (labile union) onto the surface of the implant. In order to bind IP6 covalently onto a metallic surface there have been developed and optimized organic reactions in the solid-liquid interphase and it has been successfully produced an implant comprising covalently bound IP. Moreover, it has been shown that chemically pretreated Ti coins are able to bind a higher amount of IP6, being the passivation treatment the one yielding a higher deposition of IP6.

Example 5

Effect of Phytic Acid on Osteoclastogenesis In Vitro

The effect of IP6 on cell viability, proliferation and differentiation of the RAW 264.7 monocyte/macrophage mouse cell line to differentiated osteoclasts was tested. Undifferentiated OCLs treated with IP6 were tested for specific differentiation and functional markers using real-time RT-PCR and TRAP-staining. Activity of OCLs was also determined by resorption of dentin discs and actin ring formation.

Materials and Methods

1. Cell Culture

The transformed murine monocytic cell line RAW 264.7 was cultured at 37° C. in 5% $CO_2$ atmosphere in Dulbecco modified Eagles medium (DMEM) supplemented with 10% fetal bovine serum and antibiotics (50 IU penicillin/ml and 50 μg streptomycin/ml).

2. Cytotoxicity Assay

RAW cells 264.7 were seeded at a density of 20,000 cells/cm2 in 24-well plate and cultured for 24 h. After cell attachment, culture media was changed and different doses of) IP6 were added. Cells were cultured for additional 24 hours and culture media was collected to test cytotoxicity (LDH activity). LDH cytotoxicity assay was performed using the Cytotoxicity Detection Kit according to the manufacturer's protocol. This colorimetric assay quantifies activity of LDH released from the cytosol of damaged cells into the supernatant and thus serves as an index of cell death.

Results were presented relative to the LDH activity in the media of control cells (low control, 0% of cell death) and of cells treated with 1% Triton X-100 (high control, 100% death) using the equation:

Cytotoxicity (%)=(exp value−low control)/(high control−low control)*100.

3. Cell Proliferation Assay

RAW cells 264.7 were seeded at a density of 2,500 cells/well in a 96-well plate and cultured for 24 h. After cell attachment, culture media was changed and different doses of IP6 were added. Cells were cultured for additional 24 hours and BrdU was added for the last 6 hours. Incorporation of BrdU was determinated by Cell Proliferation ELISA kit as described by the manufacturer.

4. Generation of Osteoclasts

Osteoclast-like cells were generated in culture from RAW 264.7 cells. 20,000 cells/cm2 were seeded in 24-well plates and placed in the CO2 incubator overnight to allow the cells to attach to the surface. After 24 h, the culture medium was replaced with media containing 100 ng/mL RANKL. Osteoclasts were successfully generated by dosing with RANKL every 48 h over the course of 5 days. To confirm the generation of multinucleated osteoclast-like cells, the cultured cells were stained for the enzyme TRAP using the TRAP-staining kit, according to the manufacturer's instructions. TRAP is the enzyme that has been used as a marker of osteoclast function for more than 20 years. TRAP-positive multinucleated osteoclasts were visualized by light microscopy and photographed. Each OCL formation assay was performed at least 3 times.

5. Effect of IP6 on OCL Formation

To examine the effect of IP6 on OCL formation, 20,000 cells/cm2 were seeded in 24-well plates and, after 24 h, the culture medium was replaced with media containing 100 ng/mL RANKL and different doses of IP6 (0.1, 1, 10, 100 µM). Treatments were added after changing the media every 48 h over the course of 5 days. The effect of IP6 on OCL formation was assessed by analysis of the number of TRAP-positive cells, gene expression levels of osteoclast and functional markers, resorption activity on dentin discs and actin ring formation.

6. RNA Isolation and RT-PCR Analysis

Total RNA was isolated with Tripure from cells treated as describe above, following the instructions of the manufacturer. RNA was quantified using a spectrophotometer set at 260 nm (Nanodrop, Thermo Fisher Scientific Inc, US).

The same amount of total RNA (1 mg) from each sample was reverse transcribed to cDNA at 37° C. for 60 minutes in a final volume of 20 ml, using High Capacity RNA to cDNA kit (Applied Biosystems, USA). Each cDNA was diluted 1/5 and aliquots, to avoid freezing and thawing cycles, were stored at −20° C. until the PCR reactions were carried out.

Real-time PCR was performed for two housekeeping genes: 18S rRNA, GAPDH; three osteoclast gene markers: TRAP, CalcR, CFMS; and four osteoclast functional markers: CtsK, MMP-9, Car2 and H+-ATPase.

Real-time PCR was performed in the Lightcycler 480® (Roche Diagnostics, Mannheim, Germany) using SYBR green detection. Each reaction contained 7 µl Lightcycler-FastStart DNA MasterPLUS SYBR Green I (containing Fast Start Taq polymerase, reaction buffer, dNTPs mix, SYBR-Green I dye and MgCl2), 0.5 µM of each, the sense and the antisense specific primers (Table 1) and 3 µl of the cDNA dilution in a final volume of 10 µl. The amplification program consisted of a preincubation step for denaturation of the template cDNA (5 min 95° C.), followed by 45 cycles consisting of a denaturation step (10 s 95° C.), an annealing step (10 s 60° C.) and an extension step (10 s 72° C.). After each cycle, fluorescence was measured at 72° C. A negative control without cDNA template was run in each assay.

To allow relative quantification after PCR, standard curves were constructed from standard reactions for each target and housekeeping genes. The crossing point readings for each of the unknown samples were used to calculate the amount of either the target or housekeeping relative to a standard curve, using the Second Derivative Maximum Method. Relative mRNA levels were calculated as the ratio of relative concentration for the target genes in the same sample using the Advanced Relative Quantification Method provided by the LightCycler 480 analysis software version 1.5 (Roche Diagnostics, Mannheim, Germany).

TABLE 1

Oligonucleotide primer pairs used for real-time RT-PCR

| Gene | Sequence |
|---|---|
| mGAPDH | Forward: 5'-ACCCAGAAGACTGTGGATGG-3' (SEQ ID NO: 1) |
| | Reverse: 5'-CAGATTGGGGGTAGGAACAC-3' (SEQ ID NO: 2) |
| m18S rRNA | Forward: 5'-GTA ACC CGT TGA ACC CCA TT-3' (SEQ ID NO: 3) |
| | Reverse: 5'-CCA TCC AAT CGGTAGTAG CG-3' (SEQ ID NO: 4) |
| mTRAP | Forward: 5'-GCGACCATTGTTAGCCACATACG-3' (SEQ ID NO: 5) |
| | Reverse: 5'-CGTTGATGTCGCACAGAGGGAT-3' (SEQ ID NO: 6) |
| mCalcR | Forward: 5'-TGGTGCGGCGGGATCCTATAAGT-3' (SEQ ID NO: 7) |
| | Reverse: 5'-AGCGTAGGCGTTGCTCGTCG-3' (SEQ ID NO: 8) |
| mCFMS | Forward: 5'-TGGATGCCTGTGAATGGCTCTG-3' (SEQ ID NO: 9) |
| | Reverse: 5'-GTGGGTGTCATTCCAAACCTGC-3' (SEQ ID NO: 10) |

TABLE 1-continued

Oligonucleotide primer pairs used for real-time RT-PCR

| Gene | Sequence | | |
|---|---|---|---|
| mCtsk | Forward: | 5'-AGCAGAACGGAGGCATTGACTC-3' | (SEQ ID NO: 11) |
| | Reverse: | 5'-TTTAGCTGCCTTTGCCGTGGC-3' | (SEQ ID NO: 12) |
| mMMP-9 | Forward: | 5'-GCTGACTACGATAAGGACGGCA-3' | (SEQ ID NO: 13) |
| | Reverse: | 5'-GCGGCCCTCAAAGATGAACGG-3' | (SEQ ID NO: 14) |
| mCar2 | Forward: | 5'-CTCTGCTGGAATGTGTGACCTG-3' | (SEQ ID NO: 15) |
| | Reverse: | 5'-CTGAGCTGGACGCCAGTTGTC-3' | (SEQ ID NO: 16) |
| mH$^+$ATPase | Forward: | 5'-ACGGTGATGTCACAGCAGACGT-3' | (SEQ ID NO: 17) |
| | Reverse: | 5'-CCTCTGGATAGAGCCTGCCGCA-3' | (SEQ ID NO: 18) |

7. Resorption Pit Assay

RAW 264.7 cells were seeded on dentine slices at a density of 20,000 cells/cm$^2$. To study the effect of IP6 on OCL formation cells were cultured with media containing 100 ng/mL RANKL and IP6 (1 µM) over the course of the entire experiment. To study the effect of IP6 on mature osteoclasts-like cells. OCLs were generated by dosing RAW 264.7 cells with RANKL over the course of 6 days and then treated with IP6 (1 µM) for 4 days.

After the culturing period, cells were removed from the dentine slices by sonication in 0.1 N NaOH for 2 minutes, stained in hematoxylin for 40 seconds and washed in distilled water. The surface of each dentine slice was examined by light microscopy for evidence of lacunar resorption and quantitative analysis of the resorption area was performed with Image J software 1.44p (NIH, USA).

8. Actin Ring Staining

RAW 264.7 cells were seeded on coverslips at concentration of 20,000 cells/cm2 and treated as described above. Then the coverslips were fixed, permeabilized with 0.1% Triton X-100 for 10 min, and stained with 50 µg/mL FITC-phalloidin for 30 minutes. Coverslips were washed in PBS and then nuclei were stained with Fluoroshield with DAPI. Actin rings were visualized by confocal microscopy and the percentage of total number of osteoclasts with actin ring, having intact (75-100%), disrupted (25-50%) and no actin ring (0-25%) was calculated by a blinded investigator.

Results

Figure 6:
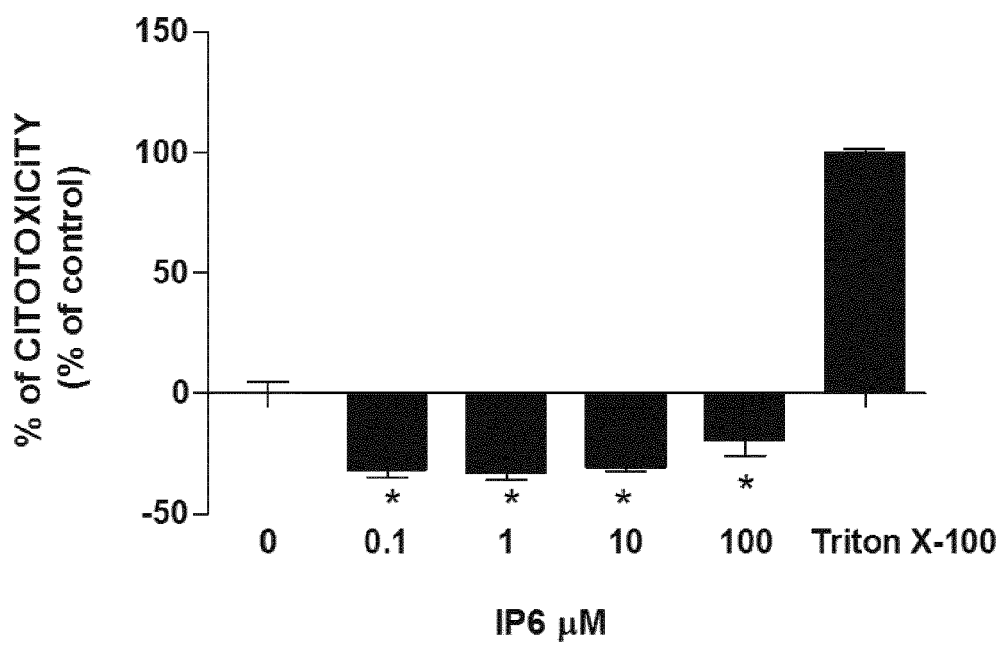
FIG. 6. Effect of IP6 on cell viability and proliferation of osteoclast progenitors cells. (A) LDH activity measured from culture media collected after treatment of cells with different doses of IP6 for 24 hours. Positive high control (100%) was culture media from cells incubated with Triton X-100 at 1%. Negative low control (0%) was culture media from control cells. Values represent the mean±SEM. Significant differences were assessed by Mann-Whitney test: *p≤0.05 versus untreated cells. (B) Proliferation of RAW 264.7 cells treated with different doses of IP6 for 24 hours and labeled with BrdU for 6 h. Values are expressed as a percentage of control cells, which were set to 100%. Values represent the mean±SEM. Significant differences were assessed by Student's t test.
Figure 6:
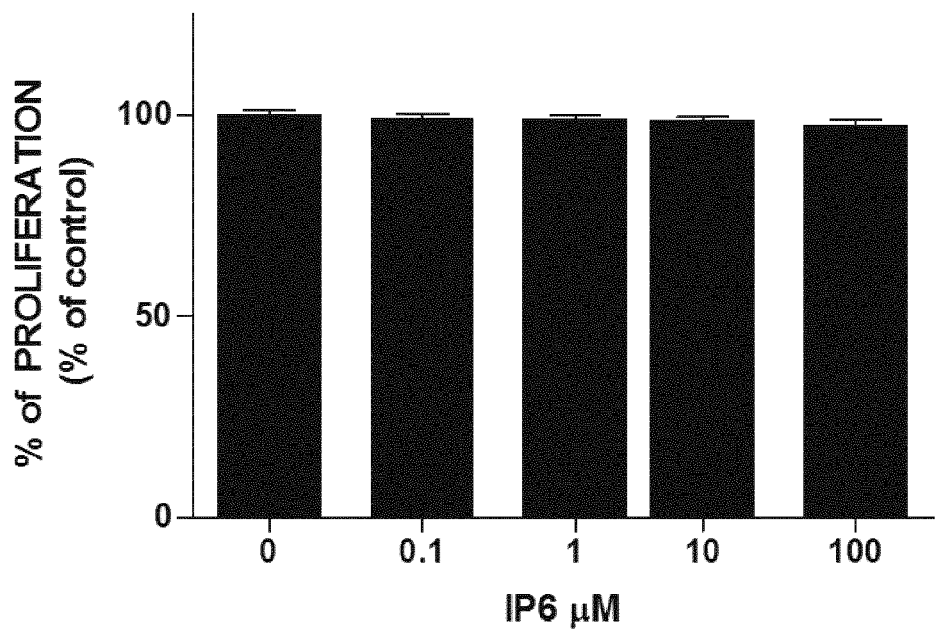
Figure 7:
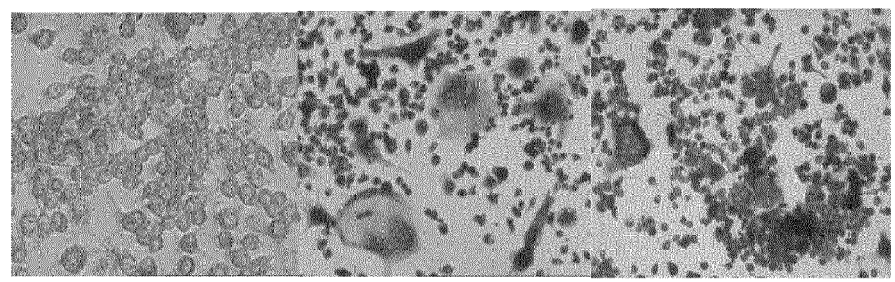
FIG. 7. IP6 directly inhibits osteoclast formation induced by RANKL. (A) Effect of IP6 treatment on the generation of multinucleated TRAP-positive cells (OCLs). RAW 264.7 cells cultured for 5 days with no stimulation with RANKL (left). RAW 264.7 dosed with 100 ng/mL RANKL for 5 days (center). RAW 264.7 cells dosed with 100 ng/mL RANKL and treated with 1 μM IP6 for 5 days (right). Representative images are shown. (B) Number of multinucleated TRAP-positive cells (OCLs) generated from RAW264.7 treated with IP6. Values are expressed as a percentage of RANKL-dosed cells non-treated with IP6, which was set to 100.
Figure 7:
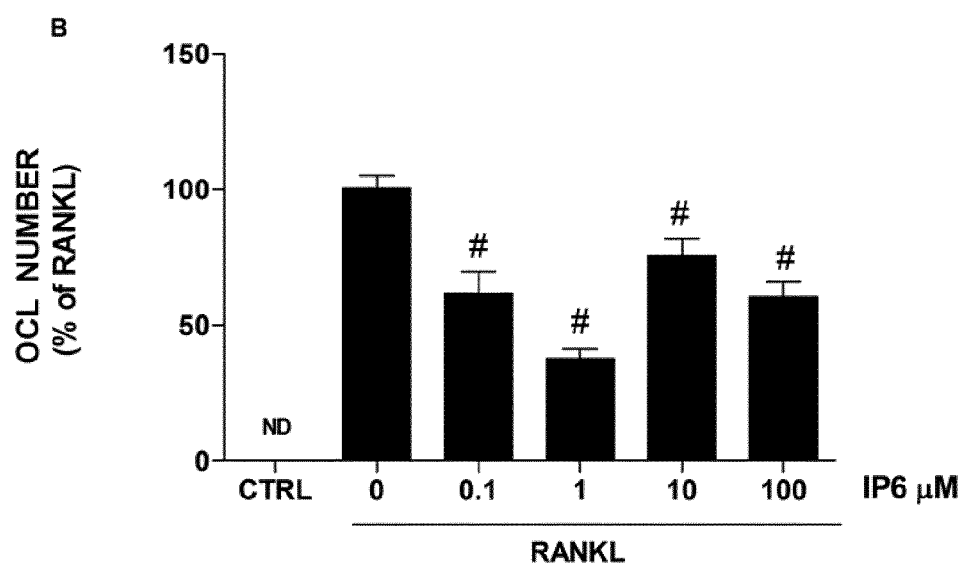
Figure 8:
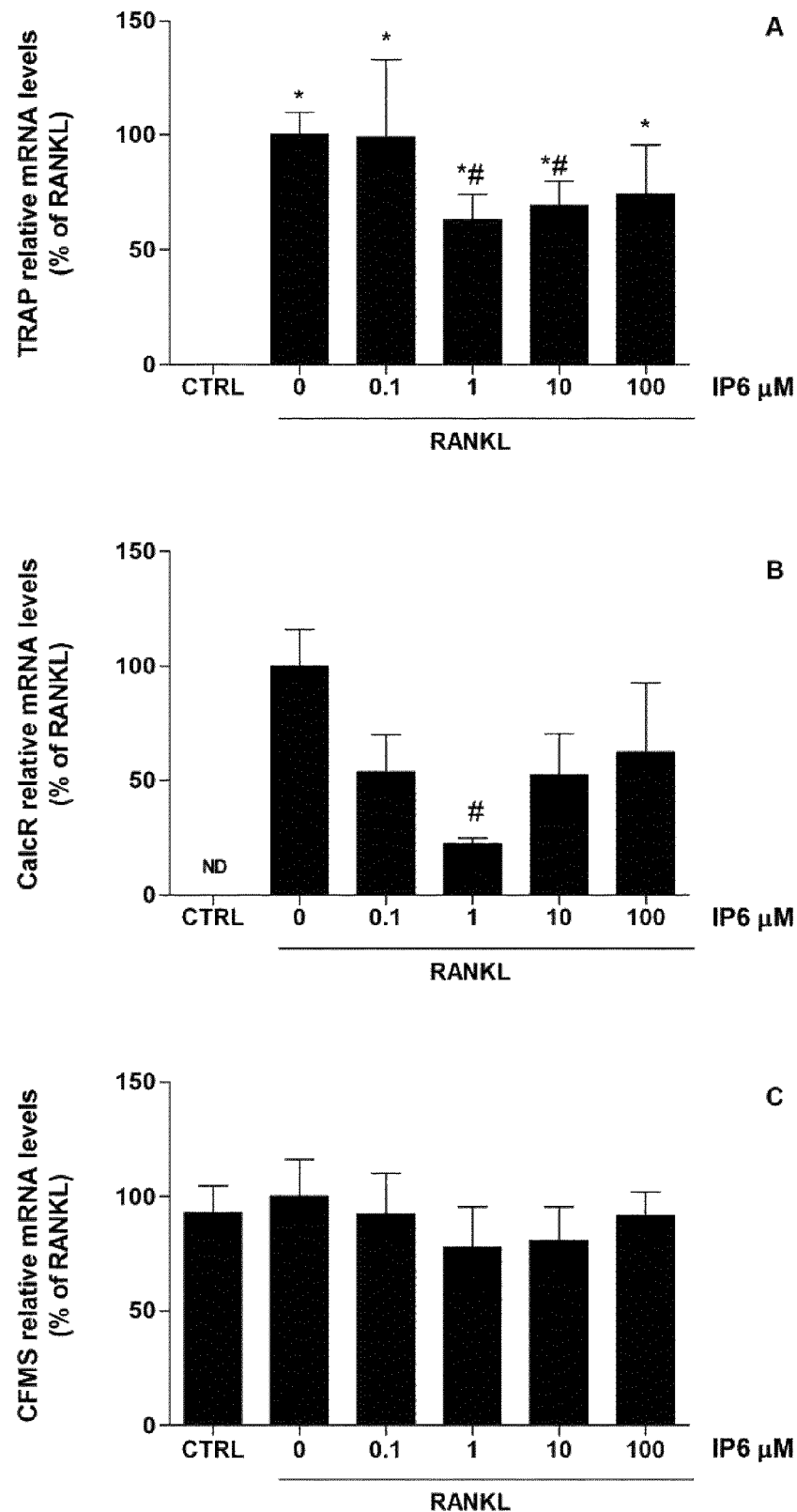
FIG. 8. IP6 directly inhibits osteoclast formation induced by RANKL. (A) TRAP mRNA levels, (C) CFMS mRNA levels and (B) CalcR mRNA levels of RANKL-stimulated cells and treated with IP6. Data represent fold changes of target genes normalized with GAPDH mRNA and 18s rRNA, expressed as a percentage of RANKL-dosed cells non-treated with IP6, which were set to 100%. Values represent the mean±SEM. Significant differences were assessed by Student's t test: *p≤0.05 versus control cells. # p≤0.05 versus RANKL treated cells.
Figure 9:
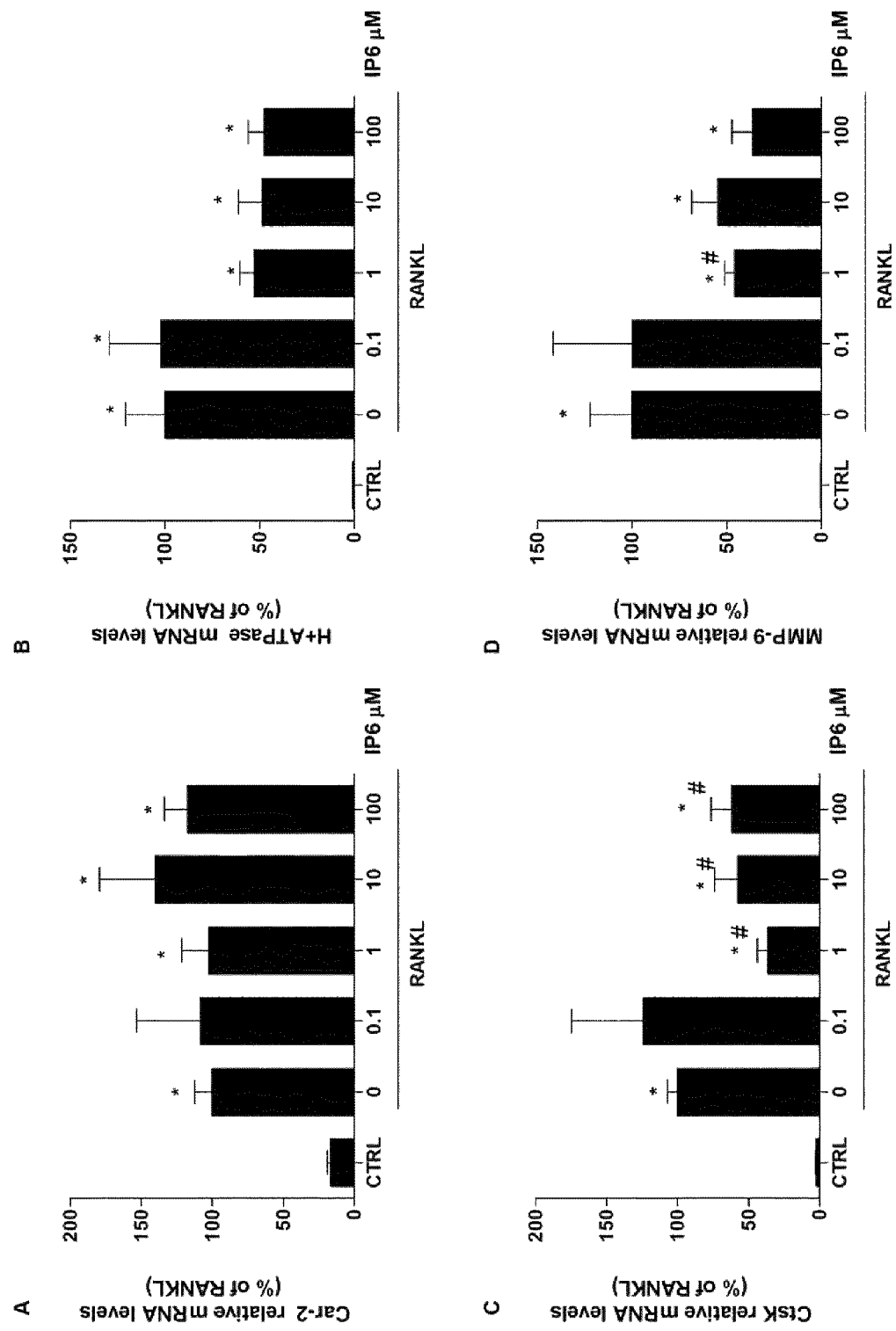
FIG. 9. IP6 directly inhibits RANKL-induced osteoclast bone resorption ability. RAW 264.7 cells were treated with RANKL (100 ng/ml) for the generation of OCLs and IP6 for 5 days and gene expression of osteoclast functional markers was determined: Car-2(A), H+-ATPase (B), CtsK (C) and MMP-9 (D). Data represent fold changes of target genes normalized with GAPDH mRNA and 18s rRNA, expressed as a percentage of RANKL-dosed cells non-treated with IP6, which were set to 100%. Values represent the mean±SEM. Significant differences were assessed by Student's t test: *p≤0.05 versus control cells. #p≤0.05 versus RANKL treated cells.
Figure 10:
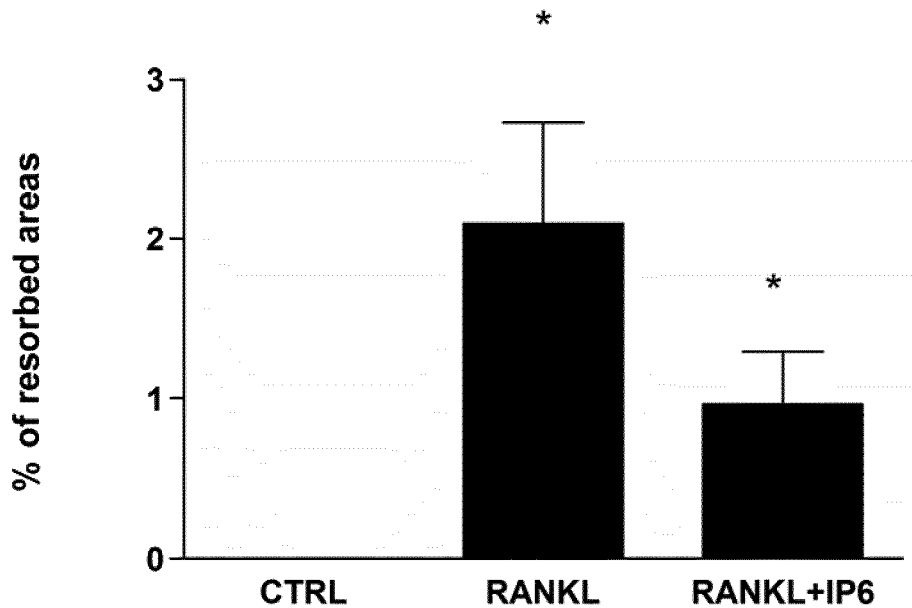
FIG. 10, IP6 directly inhibits RANKL-induced osteoclast bone resorption ability. (A) Bone resorption ability of RAW 2647 cell treated with 1 µM of IP6 during osteoclastogenesis was evaluated by resorption pit assay on dentine discs (n=3). Data represent the percentage of the resorbed area by osteoclasts. Values represent the mean±SEM. Significant differences were assessed by Student't test: *p≤0.05 versus control cells. #p≤0.05 versus RANKL treated cells. (B) Actin ring formation of mature osteoclasts treated with 1 µM of IP6 for 24 h was evaluated using confocal microscopy. Actin was stained with FITC-Phalloidin (green) and nuclei were stained with DAPI (blue). Representative images are shown.
Figure 10:
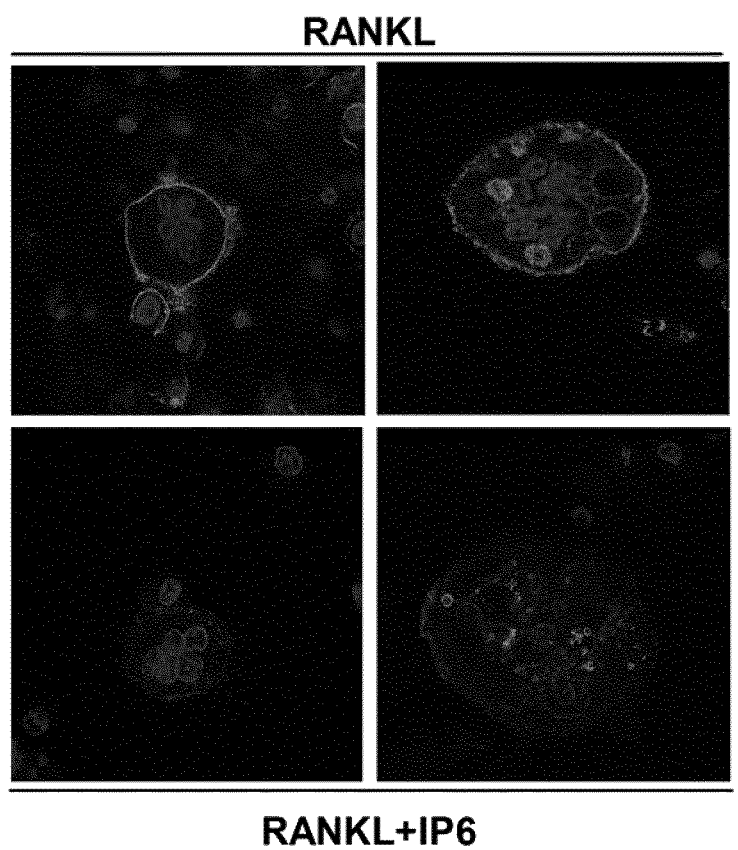

It has been shown that IP6 decreases the osteoclastogenesis in RAW 264.7 cells induced by RANKL, without affecting cell proliferation or cell viability (FIG. 6). The number of TRAP positive cells and mRNA levels of osteoclast markers such as TRAP, calcitonin receptor, cathepsin K and MMP-9 was decreased by IP6 on RANKL-treated cells (FIGS. 7 to 10). These results demonstrate that IP6 decreases the generation of mature osteoclasts without impairing their cell viability or proliferation capacity.

Example 6

Effect of Phytic Acid on Osteoblast Differentiation of Human Umbilical Cord Mesenchymal Stem Cells (hUC-MSCs) In Vitro The effect of IP6 on differentiation of human umbilical cord mesenchymal stem cells (hUC-MSCs) to osteoblasts under osteogenic conditions was tested. Mesenchymal stem cells (MSCs) can differentiate into multiple lineages such as osteoblasts, osteocytes, adipocytes, chondrocytes and early neural progenitor cells. hUC-MSC treated for 19 days with IP6 were tested for osteoblast markers using real-time RT-PCR.

Materials and Methods

1. Isolation of hUC-MSCs

Human umbilical cord derived mesenquimal stem cells (hUCMSCs) were isolated from umbilical cords obtained in the process of human umbilical cord blood donation under the Concordia Cord Blood Donation Program. The samples were obtained after informed consent and with the approval of the CEIC-IB.

To isolate hUC-MSCs, the cord was rinsed several times with sterile saline, the cord blood was drained and clots flushed from the vessels. Next, the cord was cut into small pieces and incubated with 0.075% collagenase type IA for 2 h. Then, 0.125% trypsin was added for 30 min with gentle agitation at 37° C. The digested mixture was then passed through a 100 µm filter to obtain cell suspensions. Cell pellets were resuspended in NH4Cl-based erythrocyte lysis buffer, incubated for 10 min at room temperature and washed in PBS. Finally, the cells were resuspended in DMEM-LG and 20% FBS and plated in non-coated 25 cm2 cell culture flask. Cultures were maintained in a humidified atmosphere with 5% CO2 at 37° C. After 3 days of culture the medium was replaced and non-adherent cells were removed. The medium was changed twice weekly thereafter. Once 80% confluence had been reached, adherent cells were replated at a density of 1×104 cells/cm2.

2. Cell Culture hUC-MSCs from two different donors were seeded (n=12) in 24-well plates and grown to confluence in growth media consisting of DMEM-LG supplemented with penicillin (50 IU/ml), streptomycin (50 µg streptomycin/mil) and 20% FBS. Cells were cultured at 37° C. in a humidified atmosphere of 5% CO2. At confluence (designated as day 0), cells were grown in differentiation media consisting of growth media supplemented with hydrocortisone (200 nM), ascorbic acid (50 µg/ml) and β-glycerophosphate (10 mM). Cell culture media, with or without IP6, was refreshed twice a week over a 19-day time period.

3. RNA Isolation and RT-PCR Analysis

The experimental procedure developed in example 5 was used. In this example, Real-time PCR was performed for two housekeeping genes: beta-actin, GAPDH; and four osteoblast markers: Runx2, Col1A, ALP and OC.

TABLE 2

Oligonucleotide primer pairs used for real-time RT-PCR of hUC-MSC

| Gene | Sequences |
|---|---|
| hGAPDH | Forward: 5'-TGCACCACC-AACTGCTTAGC-3' (SEQ ID NO: 19)<br>Reverse: 5'-GGCATGGACTGTGGTCATGAG-3' (SEQ ID NO: 20) |
| hbeta-actin | Forward: 5'-AAGGGACTTCCTGTAACAATGCA-3' (SEQ ID NO: 21)<br>Reverse: 5'-CTGGAACGGTGAAGGTGACA-3' (SEQ ID NO: 22) |
| hRunx2 | Forward: 5'-CTGTGCTCGGTGCTGCCCTC-3' (SEQ ID NO: 23)<br>Reverse: 5'-CGTTACCCGC-CATGACAGTA-3' (SEQ ID NO: 24) |
| hCol1A | Forward: 5'-CCTGACGCACGGCCAAGAGG-3' (SEQ ID NO: 25)<br>Reverse: 5'-GGCAGGGCTCGGGTTTCCAC-3' (SEQ ID NO: 26) |
| hALP | Forward: 5'-CCGCTATCCTGGCTCCGTGC-3' (SEQ ID NO: 27)<br>Reverse: 5'-GGTGGGCTGGCAGTGGTCAG-3' (SEQ ID NO: 28) |
| hOC | Forward: 5'-GAAGCCCAGCGGTGCA-3' (SEQ ID NO: 29)<br>Reverse: 5'-CACTACCTCGCTGCCCTCC-3' (SEQ ID NO: 30) |

Results

Figure 11:
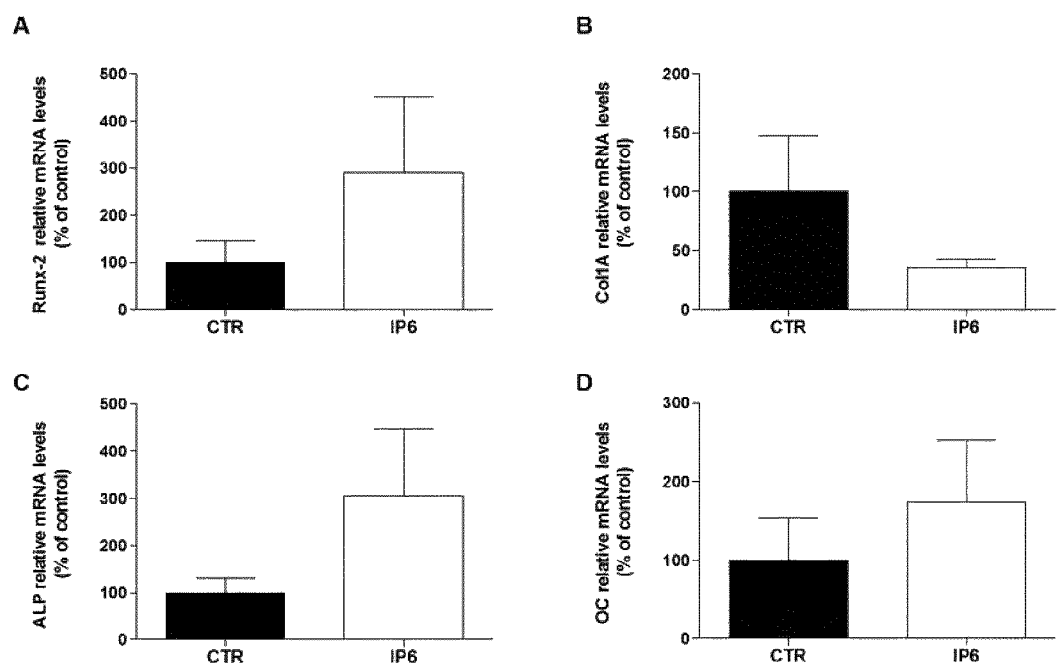
FIG. 11. IP6 induces osteoblast differentiation of hUC-MSCs. hUC-MSC cells were treated with 4 µM IP6 for 19 days and gene expression of osteoblast markers: Runx-2(A), Col1A (B), ALP (C) and OC (D) was determined. Data represent fold changes of target genes normalized with GAPDH mRNA and beta-actin mRNA, expressed as a percentage of control cells, which were set to 100%. Values represent the mean±SEM. Significant differences were assessed by Student's t test.

It has been shown that IP6 treatment induces higher mRNA levels of Runx-2, ALP, and OC compared to the control group. While, Col1A mRNA levels are lower in IP6 treated cells than in the control group (FIG. 11). Col1A is a markers for proliferation and its levels are known to decrease once the differentiation of osteoblastic cells has started. These results indicate that IP6 treatment increases osteoblast differentiation of hUC-MSCs.

Example 7

Effect of Phytic Acid-Coated Titanium Implants (Covalently Bound with a Linker and Chemically Pre-Treated) on the Biological Response of Osteoclasts In Vitro The same procedure as Example 5 can be applied to covalently attached phytic acid to titanium implants (prepared as described in examples 1 and 4).

Example 8

Effect of Phytic Acid-Coated Titanium Implants (Covalently Bound with a Linker and Chemically Pre-Treated) on the Biological Response of Osteoblasts In Vitro The effect of covalently attached phytic acid to titanium implants on cell viability and the expression of osteoblast markers on osteoblast-like cells (MC3T3-E1) was tested.
Materials and Methods
1. Covalent Binding of IP6

Phytic acid can be covalently attached to titanium implants as described in examples 1 and 4. Three types of titanium coins were tested, that were prepared as described in examples 1 and 4, titanium coins, pre-treated titanium coins (passivated) and linked with APTES and pre-treated titanium coins (passivated) and linked with APTES and IP6.
2. Cell Culture The mouse osteoblastic cell line MC3T3-E1, was maintained in α-minimum essential media supplemented with 10% fetal bovine serum and 1%-penicillin-streptomycin at 37° C. in a humidified atmosphere of 5% CO2. To test the different surface modification of titanium implants, coins were placed in a 96-well plate and $10^4$ cells were seeded on each coin.

3. Cytotoxicity Assay

LDH citotoxicity assay was performed as in example 5. Results were presented relative to the LDH activity in the media of cells cultured onto control Ti implants (low control, 0% of cell death) and of cells treated with 1% Triton X-100 (high control, 100% death) using the equation:

Cytotoxicity (%)=(exp value−low control)/(high control−low control)*100.

4. RNA Isolation and RT-PCR Analysis

Figure 12:
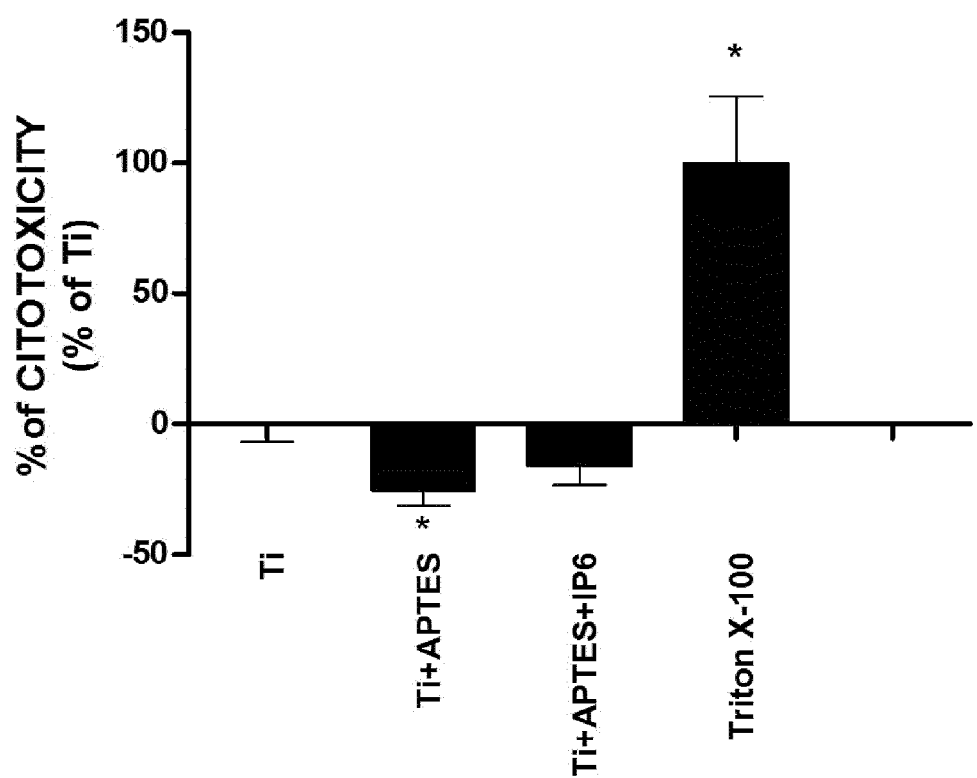
FIG. 12. Toxicity of surface modifications relative to control untreated Titanium implants (0% toxicity) and 0.1% Triton X-100 (100% toxicity) as measured by LDH-level on the respective surfaces. Three types of titanium coins were tested, control titanium coins, pre-treated titanium coins (passivated) and linked with APTES and pre-treated titanium coins (passivated) and linked with APTES and IP6. Values represent the mean±SEM. Significant differences were assessed by Student's t test: *p≤0.05 versus control Ti.
Figure 13:
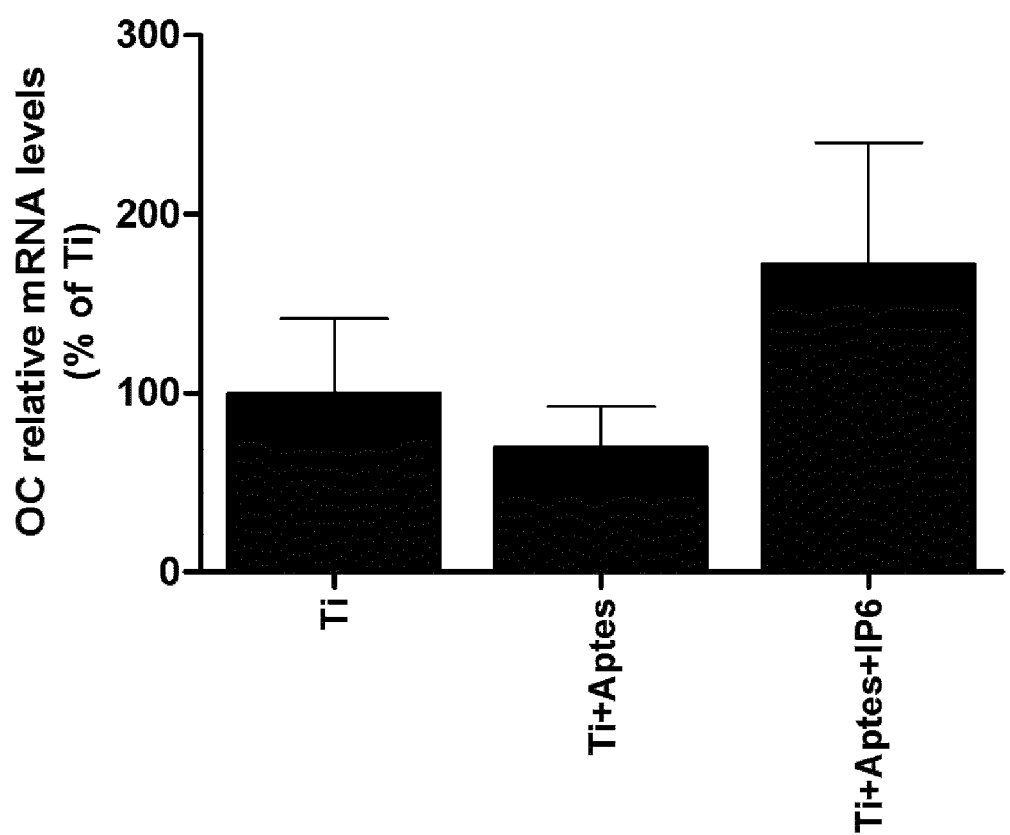
FIG. 13. Covalently attached phytic acid to titanium implants induces Osteocalcin gene expression in MC3T3-E1 cells. Data represent fold changes of osteocalcin normalized, expressed as a percentage of cells cultured onto control Ti implants, which were set to 100%. Values represent the mean±SEM. Significant differences were assessed by Student's t test.

The experimental procedure developed in example 5 was used. In this example. Real-time PCR was performed for two housekeeping genes: GAPDH (SEQ ID 1 & 2); and the osteoblast marker osteocalcin (Forward: 5'-CCGGGAGCA-GTGTGAGCTTA-3' (SEQ ID NO:31), Reverse: 5'-TAGAT-GCGTTTGTAGGCGGTC-3' (SEQ ID NO:32).
Results It has been shown that covalently attached phytic acid to titanium implants is non-toxic to the cells (FIG. 12). Moerover, an increase in osteocalcin mRNA levels induced by IP6 covalently bound to Ti implants compared to control Ti implants and to passivated Ti implants and linked with APTES (without IP6) was found (FIG. 12). These results indicate that IP6 covalently bound to Ti implants increases osteoblast differentiation.

Example 9

Effect of Phytic Acid-Coated Titanium Implants (Covalently Bound with a Linker and Chemically Pre-Treated) on the Biological Response of In Vivo The effect of covalently attached phytic acid to titanium implants can be tested in an in vivo animal model. The model of choice is a pull-out model in the proximal tibia of New Zealand White rabbits. The model uses coin-shaped implants modified only on the test side, which are in contact with cortical bone. On the opposite side a threaded hole allows for attachment of a calibrated pull-out jig. When force is applied from the jig perpendicular to the test surface of the implant, it is possible to record bone attachment without influence of friction or mechanical interlocking.
Materials and Methods
1. Covalent Binding of IP6

Three types of titanium coins can be tested, that can be prepared as described in examples 1 and 4, pre-treated titanium coins (passivated), pre-treated titanium coins (passivated) and linked with APTES and re-treated titanium coins (passivated) and linked with APTES and IP6.

2. Animals and Surgical Procedure

Six (6) New Zealand White female rabbits, 6 months old and 3.0-3.5 kg, can be used in the study (ESF Produkter Estuna AB, Norrtaïje, Sweden). The animals can be kept in cages during the experimental period. Room temperature can be regulated to 19±1° C. and humidity was 55±10%.

The experiments can be performed once they have been approved by the Norwegian Animal Research Authority and registered by this authority. The procedures have thus to be conducted in accordance with the Animal Welfare Act of Dec. 20, 1974, No 73, Chapter VI, Sections 20-22 and the Regulation on Animal Experimentation of Jan. 15, 1996. The rabbits can be sedated by injection with 0.05-0.1 ml/kg s.c. fluanisone/fentanyl (Hypnorm®, Janssen, Belgium) and 2 mg/kg bw i.v. Midazolam ten minutes prior to removal from the cages. With any signs of waking up, diluted Hypnorm® is injected slowly i.v. until adequate effect is achieved. Lidocain/adrenalin 1.8-ml s.p. can be administered locally at the operation site. Before surgery the operation sites can be depilated and washed with soft soap. Animals can be placed on their back on the operation table, covered with sterile cloths and the operating sites can be disinfected with Chlorhexidingluconat 5 mg/ml. An incision can be made on the proximal-anterior part of tibiae, penetrating all soft tissue layers. The periosteum can be elevated and retained by a self-retaining retractor. Four guide holes can be made with a twist drill (Medicon® CMS, Tuttlingen, Germany) using a drill guide to ensure standardised and correct positioning. A custom made stainless steel bur (diameter 6.25 mm) mounted in a slow-speed dental implant drill can be used for making a platform for titanium implants. Titanium coins (as described in examples 1 and 4) can than be placed into following a randomized scheme. All grinding of the bone can be done with copious physiological saline solution irrigation. Titanium coins can be covered with a teflon cap and a pre-shaped titanium maxillofacial bone plate (Medicon® CMS, Tuttlingen, Germany) retained with two titanium screws (Medicon® CMS, Tuttlingen, Germany) situated on the cortical bone as stabilizer. The soft tissue can be repositioned and sutured with Dexon® II, (Sherwood-Davis & Geek, UK).

Following surgery, each animal can receive an s.c. injection with 20 ml NaCl warmed to body temperature and buprenorphin 0.02-0.05 mg/kg s.c. A second injection of Temgesic, also 0.05 mg/kg s.c. can be given at least 3 hours after the first/previous Temgesic injection. Health condition can be monitored during the study period and the operation sites can be carefully examined daily until wound healing is complete.

3. Tensile Test and Molecular Analysis

Evaluation of the implants using the tensile test can be performed 8 weeks after the surgery. After a healing period of eight weeks, rabbits can be euthanised using fluanison/fentanyl 1.0 ml i.v. followed by pentobarbital 1 ml/kg body weight i.v. Immediately after euthanisation, an incision can be made through the soft tissue on the tibial bone. The titanium plate covering the implants can be exposed and removed. A hole can be made in the centre of the Teflon caps with a hollow needle, and pressurised air can be applied to remove the caps and expose the reverse part of the titanium implant.

The tensile tests can be performed with a Lloyds LRX Materials testing machine (Lloyds Instruments Ltd, Segensworth, UK) fitted with a calibrated load-cell of 100 N. Cross-head speed range can be set to 1.0 mm/min. The load can be applied until loosening of the implant and recorded on a load versus time plot.

After implant detachment, wound fluid from the implant site can be collected for lactate dehydrogenase activity analysis. Peri-implant bone tissue composition can be characterized based on total protein and volumetric bone mineral density (vBMD). Gene expression of molecular markers related to bone formation, resorption and inflammation can as well be evaluated.

Example 10

Covalent Binding of Phytic Acid to Titanium Implants Using a Linker—Process Optimization The following procedure can be used in order to optimize the functionalization of titanium surfaces with IP6 through covalent linking, obtaining homogeneously IP6 coated titanium surfaces in a more reproducible way.

The working protocol is described below.

Titanium surface activation: any of the experimental procedures developed in example 3 were used. After the treatment, the implants were dried in a nitrogen stream immediately prior to performing the formation of the monolayer.

Silanization: this step was performed using the experimental procedures developed in example 1. However, the formation of the APTES self-assembled monolayer was achieved in a glovebox under an atmosphere of dry nitrogen and using a 2% (v/v) APTES solution prepared in anhydrous toluene as solvent. Individual containers were used for each implant (3 ml/implant). The reaction was allowed to develop for 24 h at room temperature. Afterwards, rinse under flowing toluene (under $N_2$ atm), to remove excess silane and avoid polymerization and, outside the glovebox, rinse with acetone and ethanol to remove physisorbed material. Finally, dry at 70° C.

Covalent binding of IP6: this step was performed using the experimental procedures developed in example 1, optimized according to the following procedure:
1) Immerse the silanized implants in an aqueous solution of EDC 6 mg/ml and IP6 1 mg/ml in individual vials (3 ml/implant). 1 mg IP6=1.423 mg IP6Na6.
2) Immediately add 3 ml of imidazole solution 6 mg/ml at pH=6 to each vial.
3) Sonicate 2 h@RT
4) Rinse gently with water to remove non-reacted materials.
5) Dry with $N_2$.
6) Store in dry and fresh conditions ($N_2$ atmosphere, −20° C.).

REFERENCES

Grases, F., P. Sanchis, et al. (2010). "Effect of tetracalcium dimagnesium phytate on bone characteristics in ovariectomized rats." *J Med Food* 13(6): 1301-1306.

Liu, X. Y., P. K. Chu, et al. (2004). "Surface modification of titanium, titanium alloys, and related materials for biomedical applications." *Materials Science & Engineering R—Reports* 47(3-4): 49-121.

Mills, A. and S. LeHunte (1997). "An overview of semiconductor photocatalysis." *Journal of Photochemistry and Photobiology a-Chemistry* 108(1): 1-35.

Miyauchi, M., N. Kieda, et al. (2002). "Reversible wettability control of TiO2 surface by light irradiation." *Surface Science* 511(1-3): 401-407.

Nakamura, M., L. Sirghi, et al. (2002). "Study on hydrophilic property of hydro-oxygenated amorphous TiOx:OH thin films." *Surface Science* 507: 778-782.

Petzold, C., S. P. Lyngstadaas, et al. (2008). "UV-induced chemical coating of titanium surfaces with eicosapentaenoic acid." *Journal of Materials Chemistry* 18(45): 5502-5510.

Wang, R., K. Hashimoto, at al. (1998). "Photogeneration of highly amphiphilic TiO2 surfaces." *Advanced Materials* 10(2): 135-+.

Wu, K. R., J. J. Wang, et al. (2006). "Deposition of graded TiO2 films featured both hydrophobic and photo-induced hydrophilic properties." *Applied Surface Science* 252(16): 5829-5838.

The invention claimed is:

1. A biocompatible implant comprising one or more metal(s), metal alloy(s), metal oxide(s) or a combination thereof, wherein a compound selected from the group consisting of an inositol phosphate (IP), an ester of an IP, a pharmaceutically acceptable salt thereof or a combination thereof, is/are covalently bound, with or without a linker, to at least a part of a metal, metal alloy or metal oxide surface of said biocompatible implant, and wherein said linker is selected from the group consisting of anhydrides, alcohols, acids, amines, epoxies, isocyanates, silanes, halogenated groups, and polymerizable groups.

2. A biocompatible implant according to claim 1, wherein the IP comprises 1, 2, 3, 4, 5 or 6 phosphate groups.

3. A biocompatible implant according to claim 1, wherein a linker is bound to said metal, metal alloy or metal oxide surface and to said IP, ester of an IP, a pharmaceutically acceptable salt thereof or a combination thereof.

4. A biocompatible implant according to claim 1, wherein said metal(s), metal alloy(s) or metal oxide(s) is/are selected from the group consisting of titanium, an alloy or an oxide thereof, zirconium, an alloy or an oxide thereof, tantalum, an alloy or an oxide thereof, hafnium, an alloy or an oxide thereof, niobium, or an alloy or an oxide thereof, chromium-vanadium alloy and stainless steel.

5. A biocompatible implant according to claim 1, wherein the implant is selected from the group consisting of a surgical implant, an orthopedic implant, a dental implant, an orthopedic fixation device, an orthopedic joint replacement, a prosthetic disc for spinal fixation, or a graft material.

6. A biocompatible implant according to claim 1, wherein other biomolecules are present on a metal, metal alloy or metal oxide surface of the implant, said biomolecules being selected from the group consisting of natural biomolecules, synthetic biomolecules, and recombinant biomolecules.

7. A method for producing a biocompatible implant according to claim 1, comprising contacting and reacting an IP, an ester of an IP, a pharmaceutically acceptable salt thereof, or a combination thereof, with the surface of said biocompatible implant.

8. A method according to claim 7, comprising the steps of:
a) chemically pre-treating the surface of an implant,
b) contacting and reacting an IP, an ester of an IP, and/or a pharmaceutically acceptable salt thereof, or a combination thereof, with said chemically pre-treated surface.

9. A method according to claim 8, wherein before step b), a step of contacting and reacting a linker with said chemically pre-treated surface obtained in step a) is performed, and wherein in step b) IP is reacted with said linker.

10. A method according to claim 8, wherein step a) is performed by a passivation treatment, a piranha treatment or by treatment with one or more alkali solution(s).

11. A method according to claim 8, wherein said IP, ester of IP, pharmaceutically acceptable salt thereof or combination thereof is/are activated before being added to the surface in step b).

12. A method according to claim 11, wherein said activation is performed by adding a carbodiimide cross-linker, such as N-(3-dimethylaminopropyl)-N'-ethylcarbodiimide (EDC), to said IP, ester of IP, pharmaceutically acceptable salt thereof, or combination thereof.

13. A method for the modulation and/or improvement of osseointegration in a subject in need comprising inserting to said subject a biocompatible implant according to claim 1.

14. The method according to claim 13 comprising:
replacing bone tissue and/or restoring a function of the body of said subject, wherein said subject is a vertebrate animal.

15. A biocomptiable implant according to claim 2, wherein the IP comprises 6 phosphate groups.

16. A biocompatible implant according to claim 1, wherein said linker is 3-aminopropyltriethoxysilane (APTES).

17. A biocompatible implant according to claim 4, wherein said metal(s), metal alloy(s) or metal oxide(s) is/are selected from the group consisting of titanium, an alloy or an oxide thereof.

18. A biocompatible implant according to claim 6, wherein the biomolecules are selected from the group consisting of bioadhesives, cell attachment factors, biopolymers, blood proteins, enzymes, extracellular matrix proteins and biomolecules, growth factors and hormones, nucleic acids (DNA and RNA), receptors, synthetic biomolecules, vitamins, drugs, biphosphonates, biologically active ions, fluoride, and marker biomolecules.

* * * * *

UNITED STATES PATENT AND TRADEMARK OFFICE
CERTIFICATE OF CORRECTION

PATENT NO. : 9,433,710 B2  
APPLICATION NO. : 14/365545  
DATED : September 6, 2016  
INVENTOR(S) : Marta Monjo Cabrer et al.

Page 1 of 1

It is certified that error appears in the above-identified patent and that said Letters Patent is hereby corrected as shown below:

On the Title Page

In item [56], under Foreign Patent Documents, please delete all cited references, then enter the following:

--WO 2004024042 3/2004  
WO 2009158325 12/2009  
WO 2010134638 11/2010--

Signed and Sealed this  
Seventh Day of March, 2017

Michelle K. Lee  
*Director of the United States Patent and Trademark Office*

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Forward primer used for mGAPDH amplification

<400> SEQUENCE: 1
acccagaaga ctgtggatgg                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer used for mGAPDH amplification

<400> SEQUENCE: 2
cagattgggg gtaggaacac                                              20

<210> SEQ ID NO 3
<211> LENGTH: 20
<212> TYPE: DNA
<213> ORGANISM: Artificial Sequence
<220> FEATURE:
<223> OTHER INFORMATION: Forward primer used for m18S rRNA amplification

<400> SEQUENCE: 3
gtaacccgtt gaaccccatt                                              20

<210> SEQ ID NO 4
<211> LENGTH: 20
<212> TYPE: DNA
<213> ORGANISM: Artificial Sequence
<220> FEATURE:
<223> OTHER INFORMATION: Reverse primer used for m18S rRNA amplification

<400> SEQUENCE: 4
ccatccaatc ggtagtagcg                                              20

<210> SEQ ID NO 5
<211> LENGTH: 23
<212> TYPE: DNA
<213> ORGANISM: Artificial Sequence
<220> FEATURE:
<223> OTHER INFORMATION: Forward primer used for mTRAP amplification

<400> SEQUENCE: 5
gcgaccattg ttagccacat acg                                          23

<210> SEQ ID NO 6
<211> LENGTH: 22
<212> TYPE: DNA
```

```
<213> ORGANISM: Artificial Sequence
<220> FEATURE:
<223> OTHER INFORMATION: Reverse primer used for mTRAP amplification

<400> SEQUENCE: 6
cgttgatgtc gcacagaggg at                                              22

<210> SEQ ID NO 7
<211> LENGTH: 23
<212> TYPE: DNA
<213> ORGANISM: Artificial Sequence
<220> FEATURE:
<223> OTHER INFORMATION: Forward primer used for mCalcR amplification

<400> SEQUENCE: 7
tggtgcggcg ggatcctata agt                                             23

<210> SEQ ID NO 8
<211> LENGTH: 20
<212> TYPE: DNA
<213> ORGANISM: Artificial Sequence
<220> FEATURE:
<223> OTHER INFORMATION: Reverse primer used for mCalcR amplification

<400> SEQUENCE: 8
agcgtaggcg ttgctcgtcg                                                 20

<210> SEQ ID NO 9
<211> LENGTH: 22
<212> TYPE: DNA
<213> ORGANISM: Artificial Sequence
<220> FEATURE:
<223> OTHER INFORMATION: Forward primer used for mCFMS amplification

<400> SEQUENCE: 9
tggatgcctg tgaatggctc tg                                              22

<210> SEQ ID NO 10
<211> LENGTH: 22
<212> TYPE: DNA
<213> ORGANISM: Artificial Sequence
<220> FEATURE:
<223> OTHER INFORMATION: Reverse primer used for mCFMS amplification

<400> SEQUENCE: 10
gtgggtgtca ttccaaacct gc                                              22

<210> SEQ ID NO 11
<211> LENGTH: 22
<212> TYPE: DNA
<213> ORGANISM: Artificial Sequence
<220> FEATURE:
<223> OTHER INFORMATION: Forward primer used for mCtsk amplification

<400> SEQUENCE: 11
agcagaacgg aggcattgac tc                                              22

<210> SEQ ID NO 12
<211> LENGTH: 21
<212> TYPE: DNA
<213> ORGANISM: Artificial Sequence
<220> FEATURE:
<223> OTHER INFORMATION: Reverse primer used for mCtsk amplification

<400> SEQUENCE: 12
tttagctgcc tttgccgtgg c                                               21
```

<210> SEQ ID NO 13
<211> LENGTH: 22
<212> TYPE: DNA
<213> ORGANISM: Artificial Sequence
<220> FEATURE:
<223> OTHER INFORMATION: Forward primer used for mMMP-9 amplification

<400> SEQUENCE: 13
gctgactacg ataaggacgg ca                                              22

<210> SEQ ID NO 14
<211> LENGTH: 21
<212> TYPE: DNA
<213> ORGANISM: Artificial Sequence
<220> FEATURE:
<223> OTHER INFORMATION: Reverse primer used for mMMP-9 amplification

<400> SEQUENCE: 14
gcggccctca agatgaacg g                                                21

<210> SEQ ID NO 15
<211> LENGTH: 22
<212> TYPE: DNA
<213> ORGANISM: Artificial Sequence
<220> FEATURE:
<223> OTHER INFORMATION: Forward primer used for mCar2 amplification

<400> SEQUENCE: 15
ctctgctgga atgtgtgacc tg                                              22

<210> SEQ ID NO 16
<211> LENGTH: 21
<212> TYPE: DNA
<213> ORGANISM: Artificial Sequence
<220> FEATURE:
<223> OTHER INFORMATION: Reverse primer used for mCar2 amplification

<400> SEQUENCE: 16
ctgagctgga cgccagttgt c                                               21

<210> SEQ ID NO 17
<211> LENGTH: 22
<212> TYPE: DNA
<213> ORGANISM: Artificial Sequence
<220> FEATURE:
<223> OTHER INFORMATION: Forward primer used for mH+ATPase amplification

<400> SEQUENCE: 17
acggtgatgt cacagcagac gt                                              22

<210> SEQ ID NO 18
<211> LENGTH: 22
<212> TYPE: DNA
<213> ORGANISM: Artificial Sequence
<220> FEATURE:
<223> OTHER INFORMATION: Reverse primer used for mH+ATPase amplification

<400> SEQUENCE: 18
cctctggata gagcctgccg ca                                              22

<210> SEQ ID NO 19
<211> LENGTH: 20
<212> TYPE: DNA
<213> ORGANISM: Artificial Sequence
<220> FEATURE:

<223> OTHER INFORMATION: Forward primer used for hGAPDH amplification

<400> SEQUENCE: 19
tgcaccacca actgcttagc                                                    20

<210> SEQ ID NO 20
<211> LENGTH: 21
<212> TYPE: DNA
<213> ORGANISM: Artificial Sequence
<220> FEATURE:
<223> OTHER INFORMATION: Reverse primer used for hGAPDH amplification

<400> SEQUENCE: 20
ggcatggact gtggtcatga g                                                  21

<210> SEQ ID NO 21
<211> LENGTH: 23
<212> TYPE: DNA
<213> ORGANISM: Artificial Sequence
<220> FEATURE:
<223> OTHER INFORMATION: Forward primer used for hbeta-actin
      amplification

<400> SEQUENCE: 21
aagggacttc ctgtaacaat gca                                                23

<210> SEQ ID NO 22
<211> LENGTH: 20
<212> TYPE: DNA
<213> ORGANISM: Artificial Sequence
<220> FEATURE:
<223> OTHER INFORMATION: Reverse primer used for hbeta-actin
      amplification

<400> SEQUENCE: 22
ctggaacggt gaaggtgaca                                                    20

<210> SEQ ID NO 23
<211> LENGTH: 20
<212> TYPE: DNA
<213> ORGANISM: Artificial Sequence
<220> FEATURE:
<223> OTHER INFORMATION: Forward primer used for hRunx2 amplification

<400> SEQUENCE: 23
ctgtgctcgg tgctgccctc                                                    20

<210> SEQ ID NO 24
<211> LENGTH: 20
<212> TYPE: DNA
<213> ORGANISM: Artificial Sequence
<220> FEATURE:
<223> OTHER INFORMATION: Reverse primer used for hRunx2 amplification

<400> SEQUENCE: 24
cgttacccgc catgacagta                                                    20

<210> SEQ ID NO 25
<211> LENGTH: 20
<212> TYPE: DNA
<213> ORGANISM: Artificial Sequence
<220> FEATURE:
<223> OTHER INFORMATION: Forward primer used for hCol1A amplification

<400> SEQUENCE: 25
cctgacgcac ggccaagagg                                                    20

<210> SEQ ID NO 26
<211> LENGTH: 20
<212> TYPE: DNA
<213> ORGANISM: Artificial Sequence
<220> FEATURE:
<223> OTHER INFORMATION: Reverse primer used for hCol1A amplification

<400> SEQUENCE: 26
ggcagggctc gggtttccac                                               20

<210> SEQ ID NO 27
<211> LENGTH: 20
<212> TYPE: DNA
<213> ORGANISM: Artificial Sequence
<220> FEATURE:
<223> OTHER INFORMATION: Forward primer used for hALP amplification

<400> SEQUENCE: 27
ccgctatcct ggctccgtgc                                               20

<210> SEQ ID NO 28
<211> LENGTH: 20
<212> TYPE: DNA
<213> ORGANISM: Artificial Sequence
<220> FEATURE:
<223> OTHER INFORMATION: Reverse primer used for hALP amplification

<400> SEQUENCE: 28
ggtgggctgg cagtggtcag                                               20

<210> SEQ ID NO 29
<211> LENGTH: 16
<212> TYPE: DNA
<213> ORGANISM: Artificial Sequence
<220> FEATURE:
<223> OTHER INFORMATION: Forward primer used for hOC amplification

<400> SEQUENCE: 29
gaagcccagc ggtgca                                                   16

<210> SEQ ID NO 30
<211> LENGTH: 19
<212> TYPE: DNA
<213> ORGANISM: Artificial Sequence
<220> FEATURE:
<223> OTHER INFORMATION: Reverse primer used for hOC amplification

<400> SEQUENCE: 30
cactacctcg ctgccctcc                                                19

<210> SEQ ID NO 31
<211> LENGTH: 20
<212> TYPE: DNA
<213> ORGANISM: Artificial Sequence
<220> FEATURE:
<223> OTHER INFORMATION: Forward primer used for osteoblast marker
     osteocalcin amplification

<400> SEQUENCE: 31
ccgggagcag tgtgagctta                                               20

<210> SEQ ID NO 32
<211> LENGTH: 21
<212> TYPE: DNA
<213> ORGANISM: Artificial Sequence

```
<220> FEATURE:
<223> OTHER INFORMATION: Reverse primer used for osteoblast marker
      osteocalcin amplification

<400> SEQUENCE: 32
tagatgcgtt tgtaggcggt c                                              21
```